US009886781B2

(12) United States Patent
Goto

(10) Patent No.: US 9,886,781 B2
(45) Date of Patent: Feb. 6, 2018

(54) IMAGE PROCESSING DEVICE AND REGION EXTRACTION METHOD

(71) Applicant: HITACHI, LTD., Tokyo (JP)

(72) Inventor: Yoshihiro Goto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/764,040

(22) PCT Filed: Feb. 18, 2014

(86) PCT No.: PCT/JP2014/053678
§ 371 (c)(1),
(2) Date: Jul. 28, 2015

(87) PCT Pub. No.: WO2014/132829
PCT Pub. Date: Sep. 4, 2014

(65) Prior Publication Data
US 2016/0012614 A1    Jan. 14, 2016

(30) Foreign Application Priority Data
Feb. 28, 2013    (JP) .................................. 2013038513

(51) Int. Cl.
*G06T 7/11* (2017.01)
*A61B 6/00* (2006.01)
(Continued)

(52) U.S. Cl.
CPC ........ *G06T 11/003* (2013.01); *A61B 5/02007* (2013.01); *A61B 5/055* (2013.01);
(Continued)

(58) Field of Classification Search
CPC ......... G06T 7/0012; G06T 7/11; G06T 7/136; G06T 11/003; G06T 2207/10028;
(Continued)

(56) References Cited

U.S. PATENT DOCUMENTS

2003/0179915 A1    9/2003  Goto
2007/0244393 A1    10/2007 Oshiki et al.
(Continued)

FOREIGN PATENT DOCUMENTS

JP    4125779    4/1992
JP    2002325762  11/2002
(Continued)

OTHER PUBLICATIONS

Kotani et al., "Intravascular Ultrasound Analysis of Infarct-Related and Non-Infarct-Related Arteries in Patients Who Presented With an Acute Myocardial Infarction", Circulation. 2003;107:2889-2893.*
(Continued)

*Primary Examiner* — Katrina Fujita
(74) *Attorney, Agent, or Firm* — Cooper & Dunham LLP

(57) ABSTRACT

To provide an image processing device, a region extraction method, and an image processing method capable of extracting a target region based on minute variations in a concentration value that exist locally and clearly displaying the extracted target region, the image processing device extracts a blood vessel region A from an image to extract a region where a CT value is smaller than an average concentration value of the blood vessel region A as a soft plaque region B. For unextracted soft plaque, a pixel pair is set in a difference region between the region A and the region B, and for each pixel Pj between the pixel pairs, whether or not the pixel value is even smaller than a value slightly smaller than the CT value of the pixel pair is determined. Hence, a portion where a pixel value slightly varies locally is extracted as soft plaque.

10 Claims, 25 Drawing Sheets

(51) Int. Cl.
*A61B 5/02* (2006.01)
*G06T 11/00* (2006.01)
*A61B 5/055* (2006.01)
*G06T 7/00* (2017.01)
*G06T 7/136* (2017.01)
*A61B 6/03* (2006.01)

(52) U.S. Cl.
CPC .............. *G06T 7/0012* (2013.01); *G06T 7/11* (2017.01); *G06T 7/136* (2017.01); *A61B 6/032* (2013.01); *A61B 6/504* (2013.01); *A61B 6/5217* (2013.01); *G06T 2207/10028* (2013.01); *G06T 2207/10081* (2013.01); *G06T 2207/10088* (2013.01); *G06T 2207/20104* (2013.01); *G06T 2207/30101* (2013.01)

(58) Field of Classification Search
CPC . G06T 2207/10081; G06T 2207/10088; G06T 2207/20104; G06T 2207/30101; A61B 5/02007; A61B 5/055; A61B 6/032; A61B 6/504; A61B 6/5217
See application file for complete search history.

(56) References Cited

U.S. PATENT DOCUMENTS

| | | | | |
|---|---|---|---|---|
| 2008/0118122 A1* | 5/2008 | Sirohey | ................ | G06T 7/0012 382/128 |
| 2008/0118131 A1* | 5/2008 | Skinner | ................ | G06T 7/0012 382/131 |
| 2009/0202124 A1 | 8/2009 | Matsuda et al. | | |
| 2010/0215225 A1* | 8/2010 | Kadomura | ............ | G06T 7/0012 382/128 |
| 2011/0105902 A1* | 5/2011 | Kume | ..................... | A61B 8/14 600/443 |
| 2012/0002879 A1 | 1/2012 | Kanda et al. | | |
| 2012/0051640 A1 | 3/2012 | Kanda et al. | | |
| 2012/0078117 A1* | 3/2012 | Okada | ................. | A61B 5/0075 600/476 |
| 2012/0101391 A1* | 4/2012 | Okada | ................. | A61B 5/0075 600/476 |
| 2012/0189181 A1* | 7/2012 | Hirano | ................. | G06T 7/0012 382/128 |

FOREIGN PATENT DOCUMENTS

| | | |
|---|---|---|
| JP | 2003-175022 | 6/2003 |
| JP | 200893172 | 4/2008 |
| JP | 200982407 | 4/2009 |
| JP | 2010306 | 1/2010 |
| JP | 2011135938 | 7/2011 |
| JP | 201211137 | 1/2012 |
| JP | 201245056 | 3/2012 |
| WO | WO2005117712 A1 | 12/2005 |

OTHER PUBLICATIONS

Fukuda et al. "Predicting angiographic distal embolization following percutaneous coronary intervention in patients with acute myocardial infarction." The American journal of cardiology 91.4 (2003): 403-407.*

Hassani et al. "Negative remodeling and calcified plaque in octogenarians with acute myocardial infarction: an intravascular ultrasound analysis." Journal of the American College of Cardiology 47.12 (2006): 2413-2419.*

Kume et al. "Vulnerable carotid arterial plaque causing repeated ischemic stroke can be detected with B-mode ultrasonography as a mobile component: Jellyfish sign." Neurosurgical review 33.4 (2010): 419-430.*

Okura et al. "Incidence and predictors of plaque rupture in the peripheral arteries." Circ Cardiovasc Interv 3.1 (2010): 63-70.*

Stone et al. "Prediction of sites of coronary atherosclerosis progression: in vivo profiling of endothelial shear stress, lumen, and outer vessel wall characteristics to predict vascular behavior." Current opinion in cardiology 18.6 (2003): 458-470.*

International Search Report in PCT/JP2014/053678.

Japanese official action (and machine translation thereof) dated Oct. 31, 2017, in connection with corresponding Japanese patent application No. 2015-502868.

* cited by examiner

FIG. 3
(a)
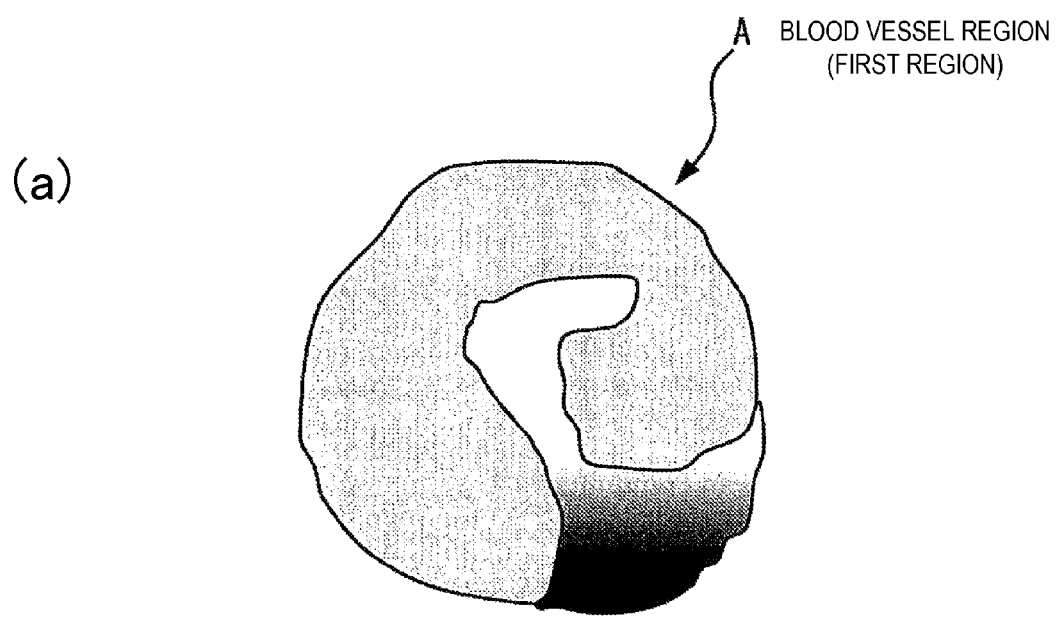
A BLOOD VESSEL REGION
(FIRST REGION)
(b)
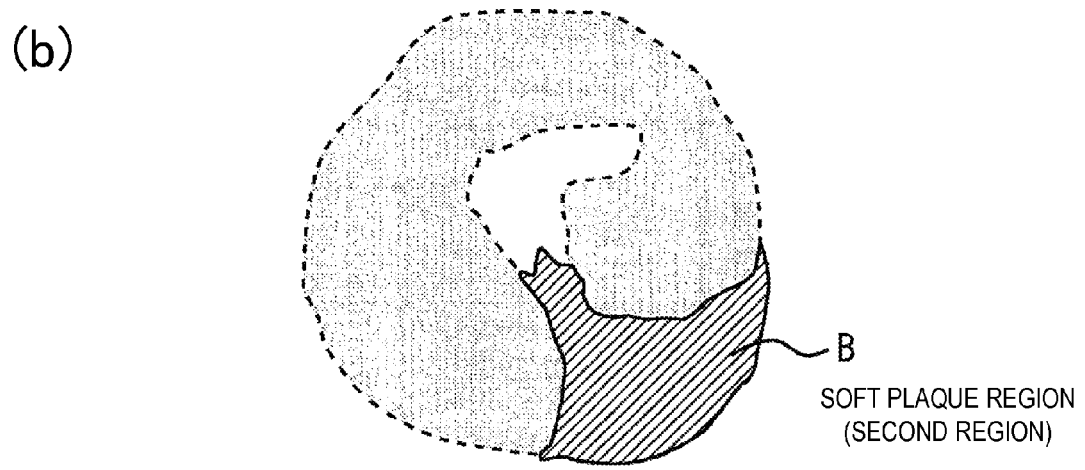
B SOFT PLAQUE REGION
(SECOND REGION)

FIG. 4
(a)
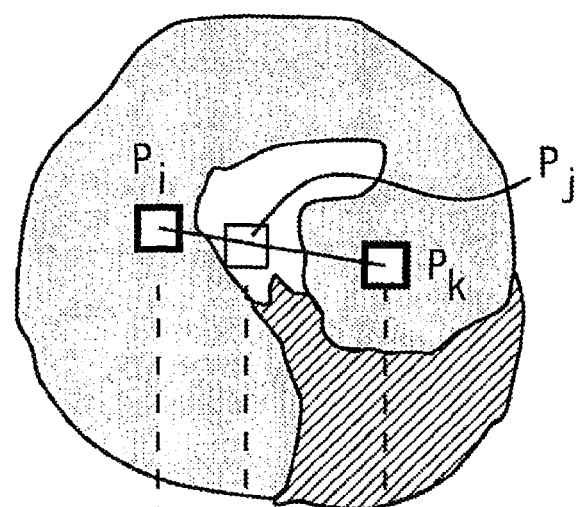
(b)
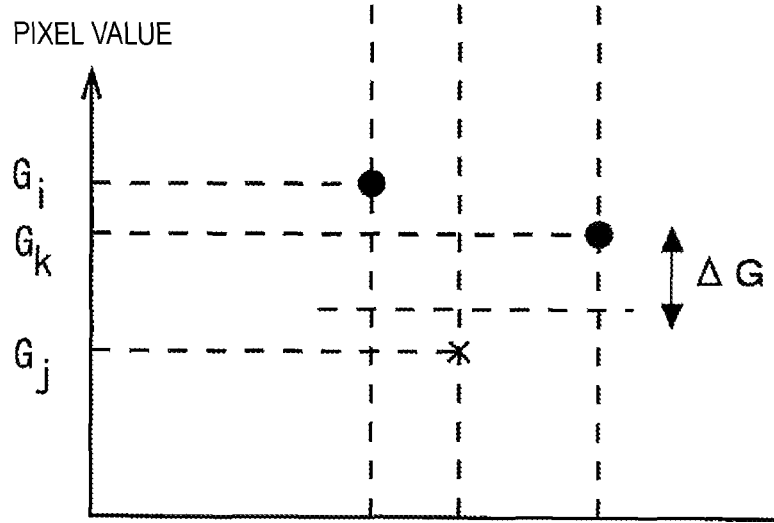

FIG. 6
(a) 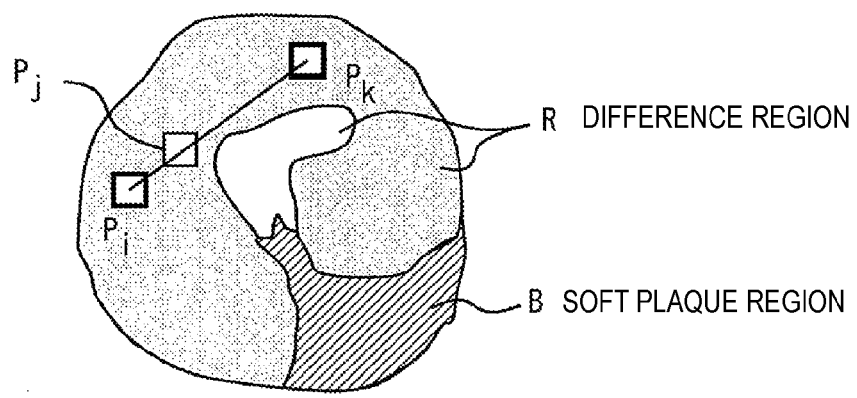
(b) 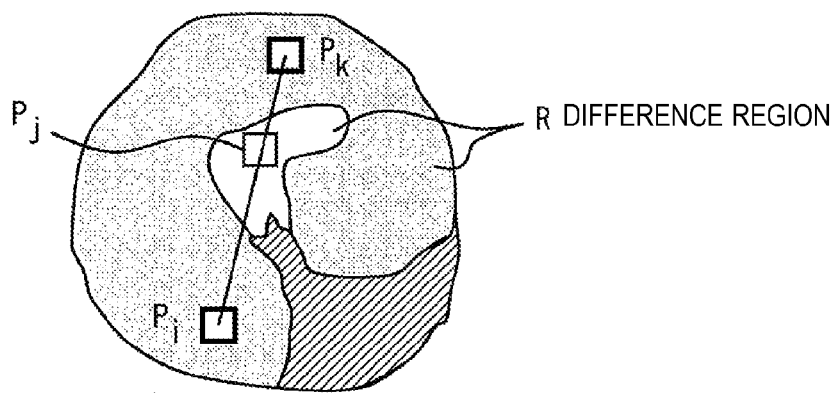
(c) 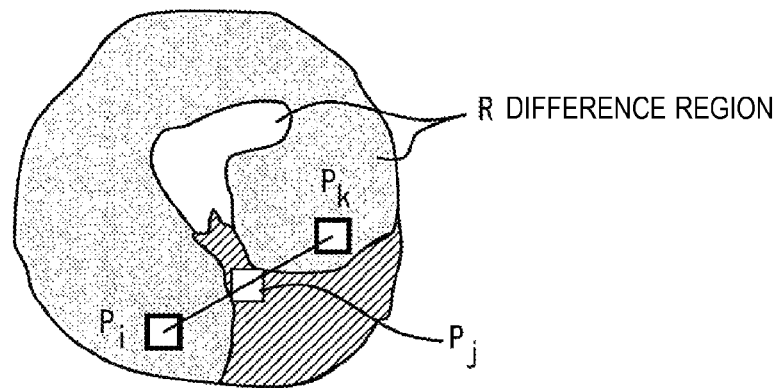

FIG. 21
(a)
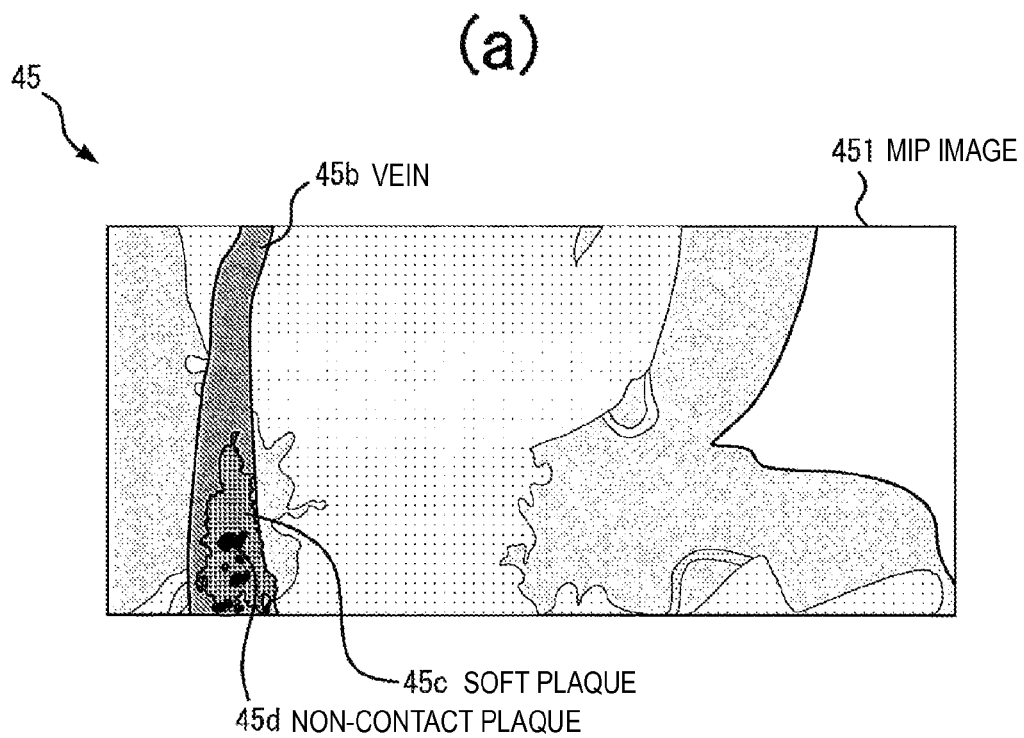
(b)
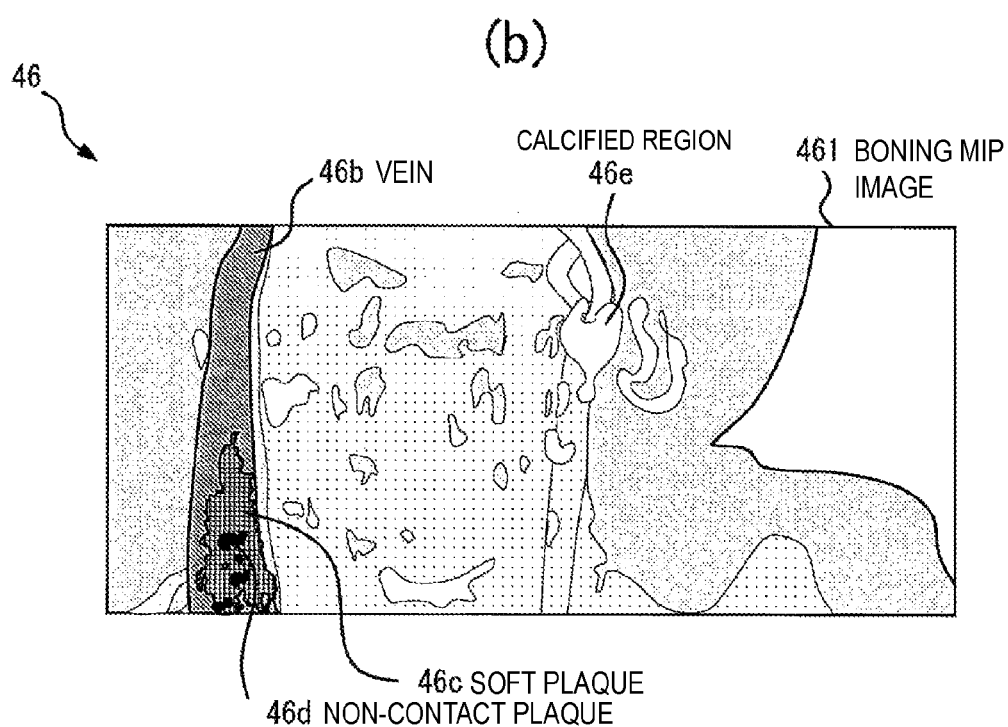

IMAGE PROCESSING DEVICE AND REGION EXTRACTION METHOD

TECHNICAL FIELD

The present invention relates to an image processing device, a region extraction method, and an image processing method and specifically relates to extraction and drawing of a vascular soft plaque in a CT image or MR image.

BACKGROUND ART

It is said that soft plaque existing in a blood vessel is unstable, easily detaches from a blood vessel wall, and has a high risk to cause a blood clot. Therefore, it is desirable that the existence and distribution of soft plaque are displayed to be easily visualized.

For example, the patent literature 1 describes an image analysis device analyzing plaque associated with a blood vessel. The image analysis device displays an index showing the plaque instability according to the pixel value distribution of an image in a designated region by designating a desired region on the image.

CITATION LIST

Patent Literature

PTL 1: Japanese Patent Application Publication No. 2011-115481

SUMMARY OF INVENTION

Technical Problem

However, it was difficult to accurately extract soft plaque from a blood vessel. Particularly, in case of a CT image, Ct values of the soft plaque and the surrounding blood are close. Because soft plaque appears as minute variations in concentration that exist locally, it was difficult to extract the soft plaque separately from the surrounding blood vessels. Also, an average CT value of an internal organ varies depending on the characteristics of a scanning device and the slice position. Therefore, there was a difficulty in setting a threshold value from the outside, and it was difficult to separate a blood vessel from the soft plaque by a simple threshold value process.

The present invention was made in light of the above problems and has a purpose to provide an image processing device and a region extraction method that are capable of extracting a target region based on minute variations of concentration values that exist locally as well as displaying the extracted target region clearly.

Solution to Problem

In order to achieve the purpose described above, the image processing device of the present invention is characterized by comprising an input unit for inputting image data, a first region extracting unit for extracting a first region from the image data input from the input unit, a second region extracting unit for performing a threshold value process for the first region using a threshold value based on a concentration in the first region to extract a second region from the first region, a third region extracting unit for setting a pixel pair that is a combination of two pixels in a difference region between the first and second regions; setting pixels between each pixel pair as pixels of interest; and then extracting the pixels of interest as a third region in a case where a difference between a pixel value of the pixel of interest and at least either pixel value of the pixel pair is larger than a predetermined value, and a target region setting unit for obtaining a region where the second and third regions are added as a target region.

Also, the image processing device is characterized by comprising a blood vessel region extracting unit for extracting a blood vessel region from an image, a soft plaque region extracting unit for extracting a soft plaque region in the blood vessel region, a shape evaluation section for evaluating a shape of the soft plaque region, a display priority setting section for setting a display priority of the soft plaque region based on the shape evaluation results of the soft plaque region, and an image generating unit for generating a two-dimensional image of the blood vessel region based on the display priority.

Also, the region extraction method of the present embodiment extracts a target region from image data using a computer and is characterized by comprising a step of inputting image data, a step of performing a threshold value process for the input image data to extract a first region, a step of performing a threshold value process for the first region using a threshold value based on a concentration in the first region to extract a second region from the first region, a step of setting a pixel pair that is a combination of two pixels in a difference region between the first and second regions; setting pixels between each pixel pair as pixels of interest; and then extracting the pixel of interest as a third region in a case where a difference between a pixel value of the pixel of interest and at least either pixel value of the pixel pair is larger than a predetermined value, and a step of obtaining a region where the second and third regions are added as a target region.

Also, the region extraction method uses a computer and is characterized by comprising a step of extracting a blood vessel region from an object image, a step of extracting a soft plaque region in the blood vessel region, a step of evaluating a shape of the soft plaque region, a step of setting a display priority of the soft plaque region based on the shape evaluation results of the soft plaque region, and a step of generating a two-dimensional image of the blood vessel region based on the display priority.

Advantageous Effects of Invention

The present invention can provide an image processing device and a region extraction method that can extract a target region based on minute variations of concentration values that exist locally as well as display the extracted target region clearly.

BRIEF DESCRIPTION OF DRAWINGS

FIG. 3 is an explanatory diagram of extracting (a): the blood vessel A and (b): the soft plaque region B.

FIG. 4(a) is a setting sample of the pixel pair (Pi, Pk), and FIG. 4(b) is a graph showing local minute variations of a pixel value.

FIG. 6 is an explanatory diagram of region extraction condition determination using pixel pairs.

FIG. 21 is an example of color-coded display according to the soft plaque shape. (a) is the display synthesized with the MIP image 451, and (b) is the display synthesized with the boning MIP image.

DESCRIPTION OF EMBODIMENTS

Hereinafter, the embodiments of the present invention will be described in detail based on the diagrams.

First Embodiment

First, referring to FIG. 1, the configuration of the image processing system 1 to which the image processing device 100 of the present invention is applied will be described.

Figure 1:
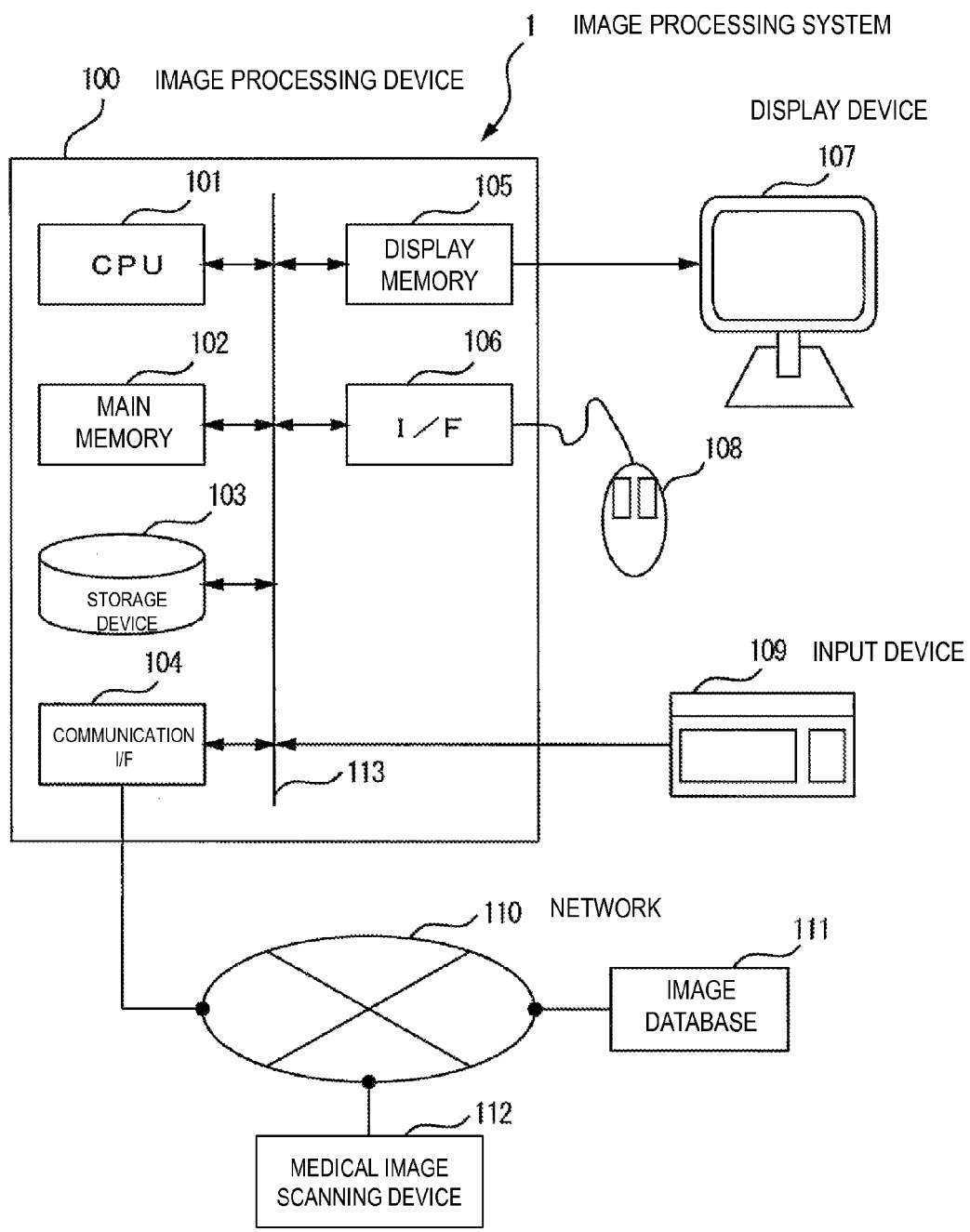
FIG. 1 is a diagram showing an overall configuration of the image processing device 100.

As shown in FIG. 1, the image processing system 1 comprises the display device 107, the image processing device 100 having the input device 109, the image database 111 to be connected to the image processing device 100 through the network 110, and the medical image scanning device 112.

The image processing device 100 is a computer performing processes such as image generation and image analysis. As shown in FIG. 1, the image processing device 100 comprises the CPU (Central Processing Unit) 101, the main memory 102, the storage device 103, the communication interface (communication I/F) 104, the display memory 105, and the interface (I/F) 106 with external devices such as the mouse 108, and each part is connected through the bus 113.

The CPU 101 executes a program to be stored in the main memory 102, the storage device 103, or the like by loading the program to a work memory region on the RAM of the main memory 102 and drives and controls each part connected through the bus 113 to achieve various processes to be performed by the image processing device 100.

The CPU 101 executes a region extraction process (See FIG. 3) extracting a soft plaque region in a blood vessel from an image. The details of the region extraction process will be described later.

The main memory 102 is composed of a ROM (Read Only Memory), a RAM (Random Access Memory), and the like. The ROM permanently holds a boot program of a computer, programs such as BIOS, data, and the like. Also, the RAM temporarily holds programs, data, and the like loaded from the ROM, the storage device 103, or the like as well as comprises a work memory region used for various processes performed by the CPU 101.

The storage device 103 is a storage device reading and writing data to an HDD (Hard Disk Drive) and the other recording media and stores programs executed by the CPU 101, data required to execute the program, an OS (Operating System), and the like. The programs including a control program equivalent to the OS and an application program are stored. These respective program codes are read by the CPU 101 as needed, are moved to the RAM of the main memory 102, and then are executed as various means.

The communication I/F 104 has a communication controller, a communication port, etc. and mediates communication between the image processing device 100 and the network 110. Also, the communication I/F performs communication control with the image database 111 and the medical image scanning device 112 such as the other computers, an X-ray CT apparatus, and an MRI apparatus via the network 110.

The I/F 106 is a port to connect peripheral devices and transmits/receives data to/from the peripheral devices. For example, it may be configured so that a pointing device such as the mouse 108 and a stylus pen is connected via the I/F 106.

The display memory 105 is a buffer temporarily accumulating display data to be input from the CPU 101. The accumulated display data is output to the display device 107 at a predetermined timing.

The display device 107 is composed of a liquid crystal panel, a display device such as a CRT monitor, and a logical circuit to execute a display process in cooperation with the display device, and is connected to the CPU 101 via the display memory 105. The display device 107 displays display data accumulated in the display memory 105 by the CPU 101 control.

The input device 109, for example, is an input device such as a keyboard and outputs various commands and information to be input by an operator to the CPU 101. The operator operates the image processing device 100 interactively using external devices such as the display device 107, the input device 109, and the mouse 108.

The network 110 includes various communication networks such as a LAN (Local Area Network), a WAN (Wide Area Network), an intranet, and the Internet and mediates communication connections between the image database 111 and a server as well as the other devices etc. and the image processing device 100.

The image database 111 accumulates and stores image data scanned by the medical image scanning device 112. Although the image processing system 1 shown in FIG. 1 has a configuration in which the image database 111 is connected to the image processing device 100 via the network 110, it may be configured so that the image database 111 is provided in, for example, the storage device 103 in the image processing device 100.

Next, referring to FIG. 2, the functional configuration of the image processing device 100 will be described.

Figure 2:
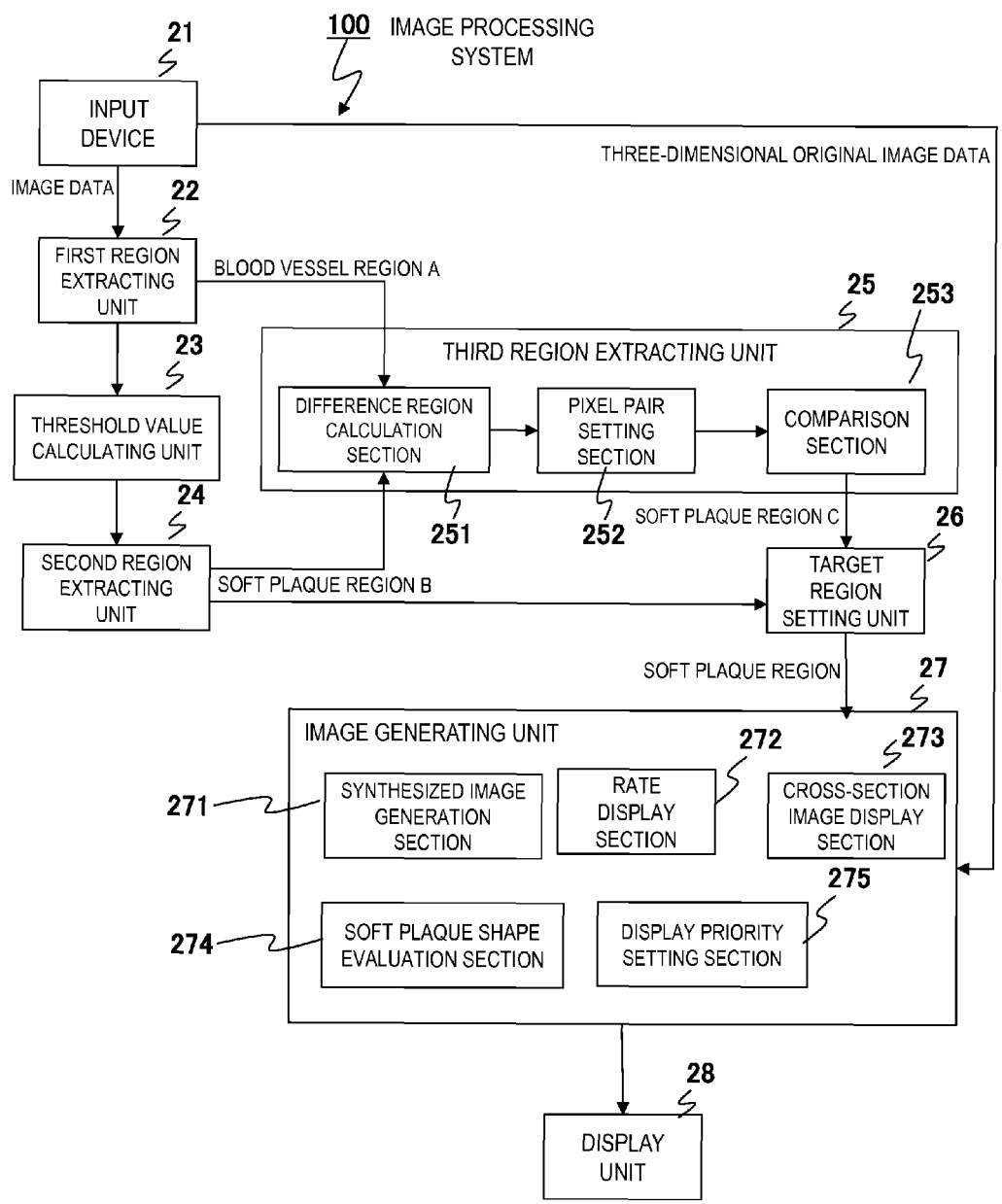
FIG. 2 is a block diagram showing a functional configuration of the image processing device 100.

As shown in FIG. 2, the image processing device 100 has the input unit 21, the first region extracting unit 22, the threshold value calculating unit 23, the second region extracting unit 24, the third region extracting unit 25, the target region setting unit 26, the image generating unit 27, and the display unit 28.

The input unit 21 inputs image data. The image data is a plurality of tomographic images scanned an object using an X-ray CT apparatus, an MRI apparatus, or the like. The plurality of accumulated tomographic images are referred to as three-dimensional original image data. Hereinafter, a case where an input image is a CT image will be described as an example.

The first region extracting unit 22 extracts a first region from image data input by the input unit 21. In the present embodiment, the first region is a blood vessel region. The first region extracting unit 22 performs a threshold value process with an appropriate threshold value to extract the blood vessel region and acquires a binary image including a plurality of blood vessels. Additionally, a particular blood vessel is extracted by specifying a roundness, location, etc. in a region. Also, the extraction method of the blood vessel region is just an example, and the other method may be used for extracting a blood vessel region.

For example, a particular blood vessel may be extracted by mouse operation of an operator. FIG. 3(*a*) is an example of the blood vessel region (first region) A extracted by the first region extracting unit 22. Because there are some cases where a blood region and soft plaque region etc. exist simultaneously in the blood vessel region (first region) A, concentration values are not always the same.

The threshold value calculating unit 23 calculates a threshold value to extract a second region based on concentration values in the blood vessel region A extracted by the first region extracting unit 22. In the present embodiment, an average concentration value of the blood vessel region A is calculated as a threshold value to extract soft plaque (a second region). Additionally, the threshold value to be calculated is not limited to the average concentration value of the blood vessel region A and may be set as the other statistic value to be calculated from concentration values in the blood vessel region A.

The second region extracting unit 24 performs a threshold value process for a first region (blood vessel region A) with a threshold value (average concentration value) calculated by the threshold value calculating unit 23 to extract a second region. For example, pixels whose pixel values are smaller than a threshold value (average concentration value) are extracted as the second region. The soft plaque region B as shown in FIG. 3(*b*) is extracted as the second region. Additionally, because there is unevenness between concentration values of soft plaque, pixels that are not extracted in the above threshold process remain even in case of soft plaque.

The third region extracting unit 25 extracts a soft plaque region (third region) that the second region extracting unit 24 failed to extract. The third region extracting unit 25 includes the difference region calculation section 251, the pixel pair setting section 252, and the comparison section 253 as shown in FIG. 2.

The difference region calculation section 251 calculates a difference region between a first region (the blood vessel region A) and a second region (the soft plaque region B). The pixel pair setting section 252 sets a pixel pair (Pi, Pk) being a combination of two pixels in the difference region. The comparison section 253 sets the pixel Pj between the pixel pair (Pi, Pk) set by the pixel pair setting section 252 as a pixel of interest and compares the pixel value Gj of the pixel of interest Pj with values (Gi−ΔG, Gk−ΔG) slightly smaller than the pixel values of the pixel pair Gi and Gk. In a case where the pixel value Gj of the pixel of interest Pj is smaller, this pixel of interest is extracted as a soft plaque region.

That is, the third region extracting unit 25 determines the following formulas (1) and (2) to extract the said pixel of interest Pj as a third region (the soft plaque region C) in case of satisfying at least either of the formulas.

$$Gj < Gi - \Delta G \tag{1}$$

$$Gj < Gk - \Delta G \tag{2}$$

FIG. 4(*a*) shows an example the pixel pair (Pi, Pk) and the pixel of interest Pj. In case of setting the pixel pair (Pi, Pk) as shown in FIG. 4(*a*) and in a case where a pixel value Gj of the pixel of interest Pj between the pixel pair (Pi, Pk) is smaller than slightly smaller values Gi−ΔG and Gk−ΔG than the pixel values of the surroundings (the pixel pair) as shown in FIG. 4(*b*), the pixel of interest Pj is extracted as a third region (soft plaque region) C.

When the value of ΔG is set to approximately 20 to 30 in case of a general contrast CT image, a desirable result can be obtained. Additionally, the value is just an example. It is desirable that a suitable value is set according to the image type, the scanning method, or the setting for an output level to the display device 107.

Figure 5:
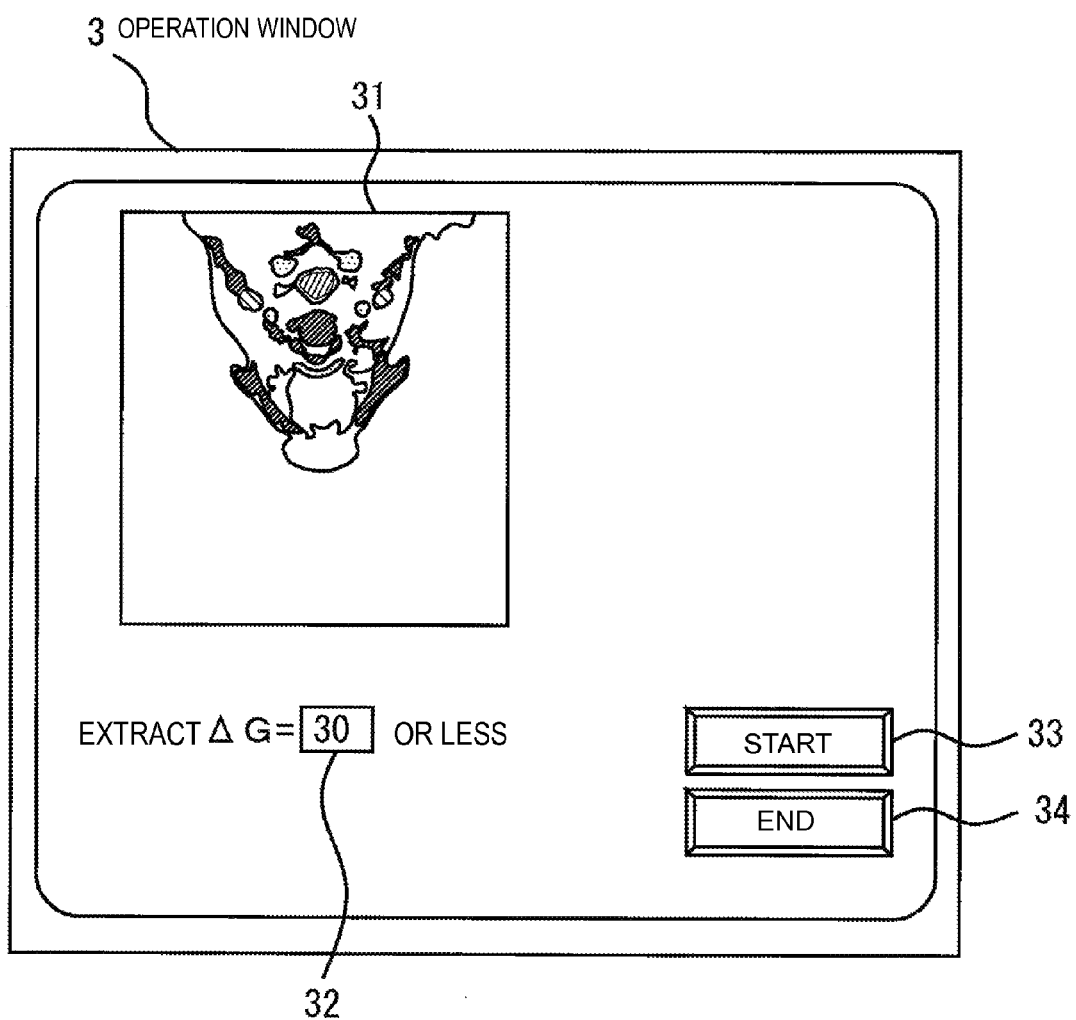
FIG. 5 is an example of the operation window 3.

It may be configured so that the value of ΔG can be set by an operator. The display unit 28, for example, displays the operation window 3 on the display device 107 as shown in FIG. 5. The operation window 3 of FIG. 5 is provided with the image display area 31 displaying an image (tomographic image) to be processed, the input field 32 for adjusting a value of the minute amount ΔG, the start button 33 commanding the start of a region extraction process, the end button commanding the completion of the region extraction process, and the like.

The third region extracting unit repeats comparing pixel values of each pixel pair in a difference region using the above conditional formulas (1) and (2).

FIG. 6(*a*) is shows a case where the pixel of interest Pj is not extracted as a third region (soft plaque region) C. When the pixel value Gj of the pixel of interest Pj between a pixel pair set in the difference region R satisfies Gj>Gi−ΔG or Gj>Gk−ΔG, the pixel of interest Pj is not extracted as soft plaque (the third region C).

FIGS. 6(*b*) and 6(*c*) show cases where the pixel of interest Pj is extracted as the third region (soft plaque region) C.

When the pixel value Gj of the pixel of interest Pj between a pixel pair set in the difference region R satisfies:

$$Gj<Gi-\Delta G \text{ or } Gj<Gk-\Delta G \text{ and}$$

$$Gj<Gi-\Delta G \text{ and } Gj<Gk-\Delta G,$$

the pixel of interest Pj is extracted as soft plaque (the third region C).

By comparing a pixel value of the pixel of interest Pj with that of the surroundings (pixel pair), local minute variations of the pixel value can be perceived relatively. Consequently, the soft plaque region C and the surrounding blood can be minutely distinguished and extracted. Also, all the targets can be searched by setting and scanning pixel pairs in a difference region.

Additionally, the above conditional formulas (1) and (2) are examples for a case where a contrast CT image is set as an input image. Because a pixel value of soft plaque appears smaller than that of a blood region in the contrast CT image, the above conditional formulas (1) and (2) are applied.

On the contrary to this, there is a case where in an MR image, the pixel value relationship between a blood region and soft plaque is inverted according to the scanning method. In an image where a pixel value of the soft plaque appears larger than that of the blood region, the following conditional formulas (3) and (4) are applied instead of the above conditional formulas (1) and (2).

$$Gj>Gi+\Delta G \quad (3)$$

$$Gj>Gk+\Delta G \quad (4)$$

In the graph of FIG. 4(b), the positive direction of the vertical axis (pixel-value axis) is reversed. Also, the second region extracting unit 24 extracts a region with a pixel value larger than a threshold value (average concentration value) as the second region B.

Figure 7:
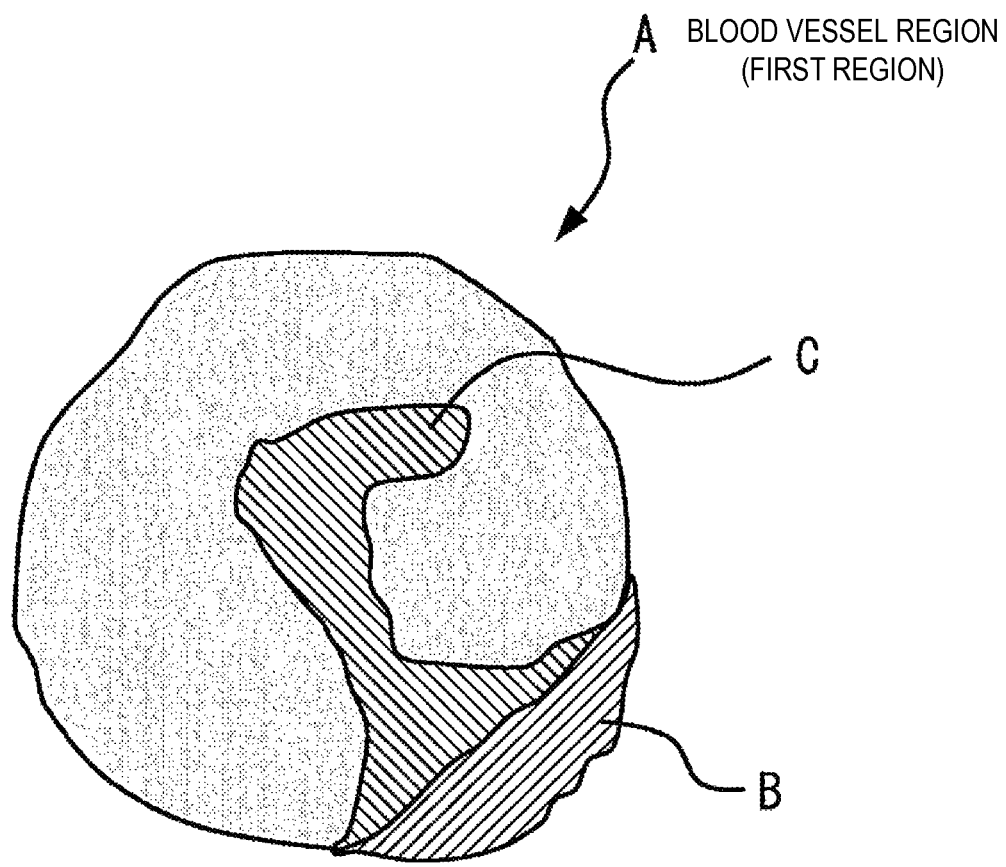
FIG. 7 is a distribution example of target regions (the soft plaque regions B and C).

The target region setting unit 26 of FIG. 2 obtains a region where the second region B and the third region C are added as a target region. The target region is a soft plaque region. FIG. 7 is a diagram schematically showing the distribution of the target regions (B and C) in the blood vessel region A.

Additionally, although the first region extracting unit 22, the second region extracting unit 24, and the third region extracting unit 25 described above write symbols to distinguish the respective regions A, B, and C for each extracted pixel in the memory, it may be configured so that the respective region extracting units 22, 24, and 25 have different memories respectively or so that sequential overwriting is performed in one memory. For example, there is a case where pixels extracted as the second region B are overwritten as the third region C by the process of the third region extracting unit 25. Eventually, a region where the second region B and the third region C are added is set as a target region.

Figure 8:
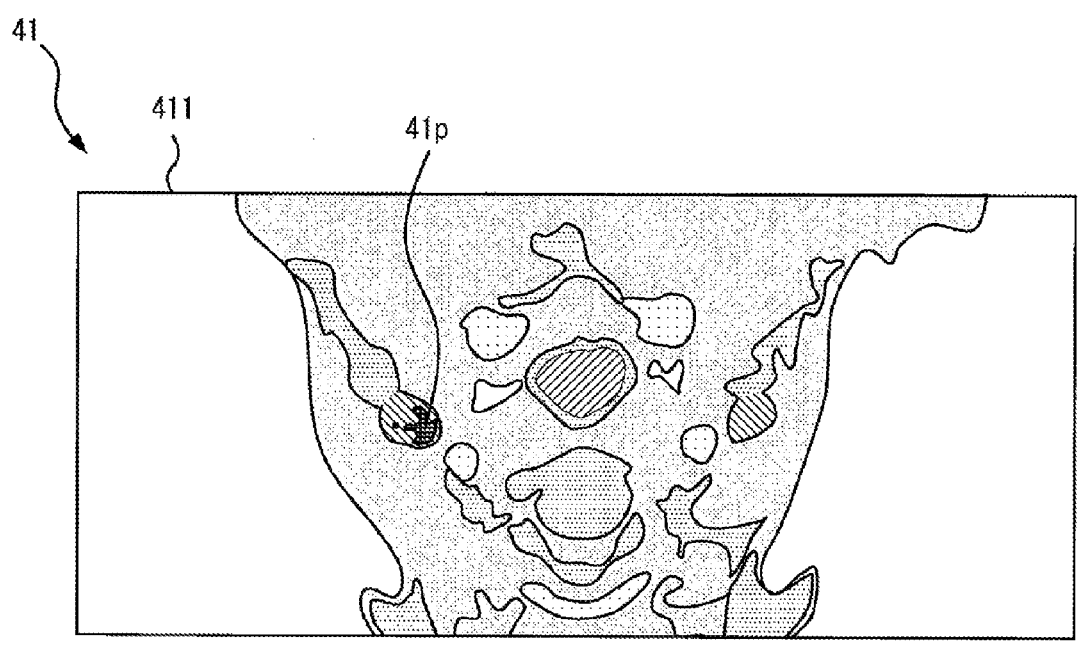
FIG. 8 is the image 41 where the extracted target region 41p is superimposed on the tomographic image 411.

The image generating unit 27 draws the extracted target region on a two-dimensional image in the surroundings and outputs it to the display unit 28. The display unit 28 displays the two-dimensional image in which the target region is drawn on the display device 107. The two-dimensional image 41 of FIG. 8 shows a case where the target region 41p is color-coded in the tomographic image 411 of the cervix of an object.

Figure 9:
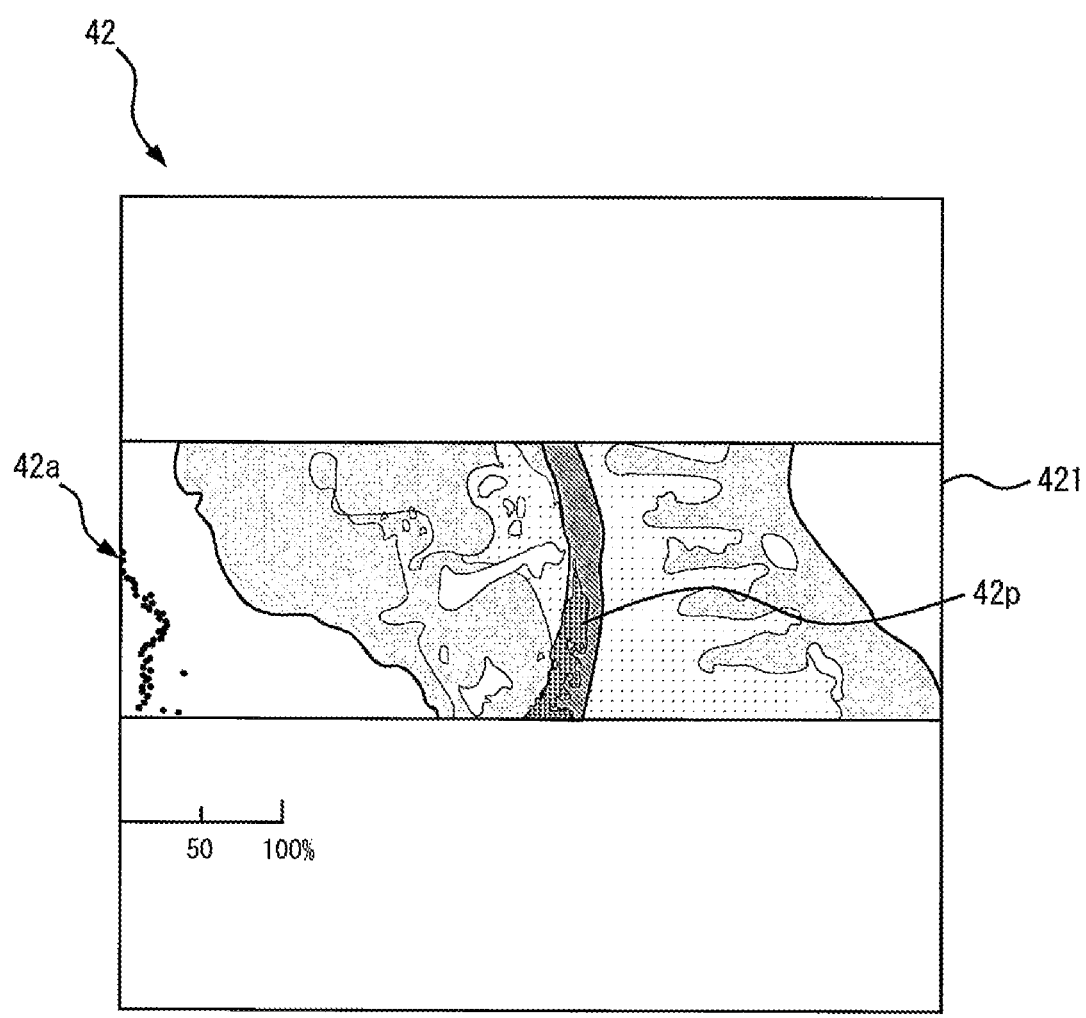
FIG. 9 shows the two-dimensional image 42 displayed by superimposing or synthesizing the extracted target region 42p on the boning MIP image 421 and an example of the area rate display 42a of soft plaque.

Also, it may be configured so that the image generating unit 27 is provided with the synthesized image generation section 271. The synthesized image generation section 271 first generates the reference two-dimensional image 421 of the surroundings of a target region based on three-dimensional image data. The reference two-dimensional image 421 shown in FIG. 9 is a boning MIP image in which the cervix of an object is projected in the lateral direction. Additionally, the synthesized image generation section 271 generates the shaded image 42p of the target region (soft plaque region). Then, the shaded image 42p of the target region is superimposed or synthesized on the reference two-dimensional image 421 to generate the synthesized image 42.

Figure 10:
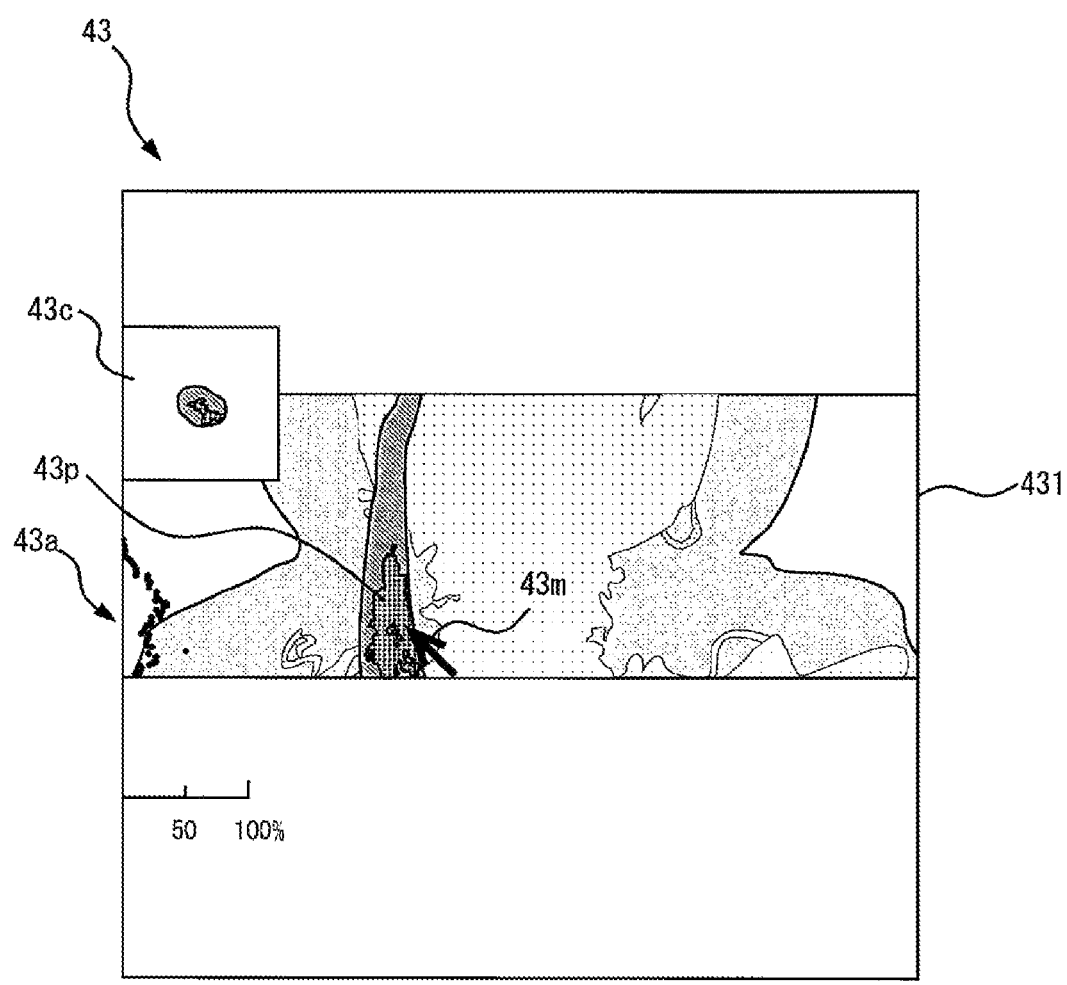
FIG. 10 shows the two-dimensional image 43 displayed by superimposing or synthesizing the extracted target region 43p on the boning MIP image 431, the cross-sectional display 43c, and an example of the area rate display 43a of soft plaque.

The reference two-dimensional image 431 of FIG. 10 is an MIP image in which an MIP (Maximum Intensity Projection) process is performed for the cervix of an object in the anteroposterior direction. In the synthesized image 43 of FIG. 10, the shaded image 43p of the target region is superimposed or synthesized on the reference two-dimensional image 431.

Additionally, the reference two-dimensional images 421 and 431 are not limited to an MIP image and a boning MIP image. The other types of two-dimensional images that can be generated from a three-dimensional image, such as an MRP (Multi-Planar Reconstruction) image, CRP (Curved Planar Reconstruction) image, 3D image, ray sum image, and MinIP image may be used.

Also, it may be configured so that the image generating unit 27 is provided with the rate display section 272. The rate display section 272 calculates an area rate at which a first region (the blood vessel region A) is occupied by a target region (soft plaque regions B and C) for each cross section and displays the rate in a graph. The vertical and horizontal axes are a cross-sectional position and a percentage (%) respectively in the rate display 42a of FIG. 9 and the rate display 43a of FIG. 10. The cross-sectional positions of the rate displays 42a and 43a correspond with the cross-sectional positions of the synthesized images 42 and 43.

Also, it may be configured so that the image generating unit 27 is provided with the cross-section image display section 273. As shown in FIG. 10, the cross-section image display section 273 generates and displays the cross-sectional image 43c orthogonal to the core line of a first region (the blood vessel region A) in a designated position when an arbitrary position of the synthesized image 43 is designated with the mouse pointer 43m etc. Moreover, the cross-section image display section 273 color-codes an extracted target region in the cross-sectional image 43c.

Also, the image generating unit 27 may be provided with the soft plaque shape evaluation section 274 and the display priority setting section 275. The soft plaque shape evaluation section 274 and the display priority setting section 275 will be described in the second embodiment.

Next, referring to the flow chart of FIG. 11, the flow of the region extraction method to be executed by the image processing device 100 of the first embodiment will be described.

The CPU 101 (the first region extracting unit 22) inputs image data of CT images etc. to be processed from the image database 111 to be connected through the storage device 103 or the communication I/F 104 (Step S101). Then, the blood vessel region A (a first region) is extracted from the input image (Step S102). The extraction of the blood vessel region A may be performed by a publicly-known method. It may be configured so that a threshold value to extract a blood vessel is input from the outside using the input device 109 etc. and so that the threshold value is set to a predetermined value. By a threshold value process, for example, the region A shown in FIG. 3(a) is extracted.

Additionally, there is a case where a binary image acquired in the threshold value process includes a plurality of blood vessels. In that case, the CPU 101 extracts a particular blood vessel from the plurality of blood vessels. For example, a particular blood vessel is extracted from a plurality of blood vessels by specifying a roundness, location, etc. of a region, and a region specified with a mouse etc. is extracted as a particular blood vessel.

Next, the CPU 101 (the threshold value calculating unit 23) calculates a threshold value to extract a soft plaque region based on pixel values in the blood vessel region A extracted in Step S102. For example, an average CT value in the blood vessel region A is calculated (Step S103). The CPU 101 (the second region extracting unit 24) extracts a region whose pixel values are smaller than the average CT value as a second region (soft plaque region) B (Step S104). For example, the second region B shown in slant lines in FIG. 3(*b*) is extracted.

It is difficult to extract all of the soft plaque in the threshold value process of Step S104.

Therefore, in the next step, soft plaque for which extraction failed is extracted by finding local concentration variations.

The CPU 101 (the third region extracting unit 25) searches for a pixel showing a CT value slightly lower than the surrounding CT values from the difference region R between the blood vessel region A and the extracted soft plaque region B. The CPU 101 first sets a pixel pair for the difference region R between the blood vessel region A and the soft plaque region B extracted in Step S104 (Step S105). Then, the CPU 101 pays attention to the pixel Pj between the pixel pair (Pi, Pk) to determine whether or not the CT value Gj of the pixel of interest Pj satisfies the following conditions (1) and (2) (in case of a CT image). When at least either condition of the following conditions (1) and (2) is satisfied, the pixel of interest Pj is extracted as the soft plaque region C (Steps S106 and S107).

$$Gj < Gi - \Delta G \quad (1)$$

$$Gj < Gk - \Delta G \quad (2)$$

The CPU 101 repeats the processes from Steps S106 to S107 while shifting the position of a pixel pair to be set in a difference region (Step S108: Yes→Step S106).

FIG. 7 shows the extraction result of the soft plaque region C through Steps S106 and S107.

A part (a region whose CT value is smaller than an average CT value of a blood vessel) of the soft plaque region B extracted in step S104 is extracted as the region C. In FIG. 7, a region including the regions B and C is a soft plaque region (target region) (Step S109).

The CPU 101 generates a tomographic image, a blood vessel cross-sectional image, or a reference image of the surroundings of an extracted target region. Additionally, the extracted target region is color-coded or shaded to display the region clearly on the reference image (Steps S110 and S111). FIG. 8 is an example where the extracted soft plaque region 41*p* is color-coded on the tomographic image 41.

For example, as shown in FIGS. 9 and 10, a reference two-dimensional image such as the boning MIP image 421 and the MIP image 431 is generated based on a three-dimensional original image, the shaded two-dimensional image 42*p* is generated for an extracted target region (soft plaque region), and then these images may be superimposed or synthesized for display.

Also, as shown in FIG. 10, the blood vessel cross-sectional image 43*c* at a position designated by the mouse pointer 43*m* may be displayed in the same display window. In the blood vessel cross-sectional image 43*c*, a soft plaque region is distinguished (for example, by color-coding) so as to display the region clearly.

Also, as shown in FIGS. 9 and 10, the CPU 101 may display a soft plaque area rate in a blood vessel cross section. A soft plaque area rate in a blood vessel in each cross-sectional position is plotted in the coordinate region in which the horizontal axis is a percentage (%) and the vertical axis is a cross-sectional position. Hence, an operator can observe soft plaque distribution on an image or quantitatively.

As described above, according to the image processing device 100 of the first embodiment, the CPU 101 extracts a region whose CT value is smaller than an average concentration value of the blood vessel region A as the soft plaque region B from the blood vessel region A extracted from an image. Also, a pixel pair is set for soft plaque that is not extracted in the difference region R between the blood vessel region A and the soft plaque region B, and whether or not each pixel Pj between the pixel pair has a pixel value further smaller than a slightly smaller value (minute value) than a CT value of the pixel pair is determined. Hence, the CPU 101 can extract local minute variations of a pixel value. This can minutely extract a soft plaque region that was difficult to separate and extract from a blood vessel region.

Second Embodiment

Next, the shape evaluation and the display mode of the extracted soft plaque will be described.

First, referring to FIG. 12, two types of soft plaque in different states will be described.

The soft plaque in the blood vessel 5 includes soft plaque having no contact with the blood vessel wall 51 and soft plaque having a contact with the wall in the cross section α. Hereinafter, the soft plaque that contacts the blood vessel wall 51 is referred to as the contact plaque 52, and the soft plaque that does not contact the blood vessel wall 51 is referred to as the non-contact plaque 53.

The non-contact plaque 53 is a soft plaque region entirely surrounded by a blood region in the cross section of interest α. This type of soft plaque tends to come off or snap off easily, which increases a pathological risk.

The contact plaque 52 is relatively stable because it adheres to the blood vessel wall 51, which results in a low risk to come off.

In the second embodiment, the image generating unit 27 of the image processing device 100 evaluates a soft plaque shape and performs image generation so as to preferentially draw the non-contact plaque 53 having a high pathological risk.

The image generating unit 27 of the image processing device 100 of the second embodiment uses the functions of the soft plaque shape evaluation section 274 and the display priority setting section 275 shown in FIG. 2. However, the other functional configuration (the input unit 21, the first region extracting unit 22, the threshold value calculating unit 23, the second region extracting unit 24, the third region extracting unit 25, and the target region setting unit 26) is the same as the image processing device 100 of the first embodiment, and the repeated descriptions are omitted. Also, the hardware configuration of the image processing device 100 is the same as the first embodiment.

The soft plaque shape evaluation section 274 determines whether or not a target region extracted by the region extraction process of the first embodiment comes into contact with the inner periphery of the first region A. That is, whether or not a soft plaque region in a blood vessel comes into contact with the blood vessel wall 51 is determined.

The display priority setting section 275 sets a display priority based on an evaluation result of the soft plaque shape evaluation section 274. In a case where a target region (soft plaque region) does not come into contact with the inner periphery (the blood vessel wall 51) of the first region A, the display priority is set so that the target region (soft plaque region) is preferentially drawn. For example, although a maximum pixel value is projected on a projection line in a normal MIP image etc., a display of the non-contact plaque 53 is prioritized in the second embodiment. Additionally, the display priority setting section 275 may set a display priority in light of the positional relationship between the point of view and the target region (soft plaque region). For example, in a case where there are two of the non-contact plaque 53 on the projection line, a display of the non-contact plaque closer to the point of view is prioritized.

Next, referring to FIGS. 13 to 20, the image generation process in the image processing device 100 of the second embodiment will be described.

Figure 11:
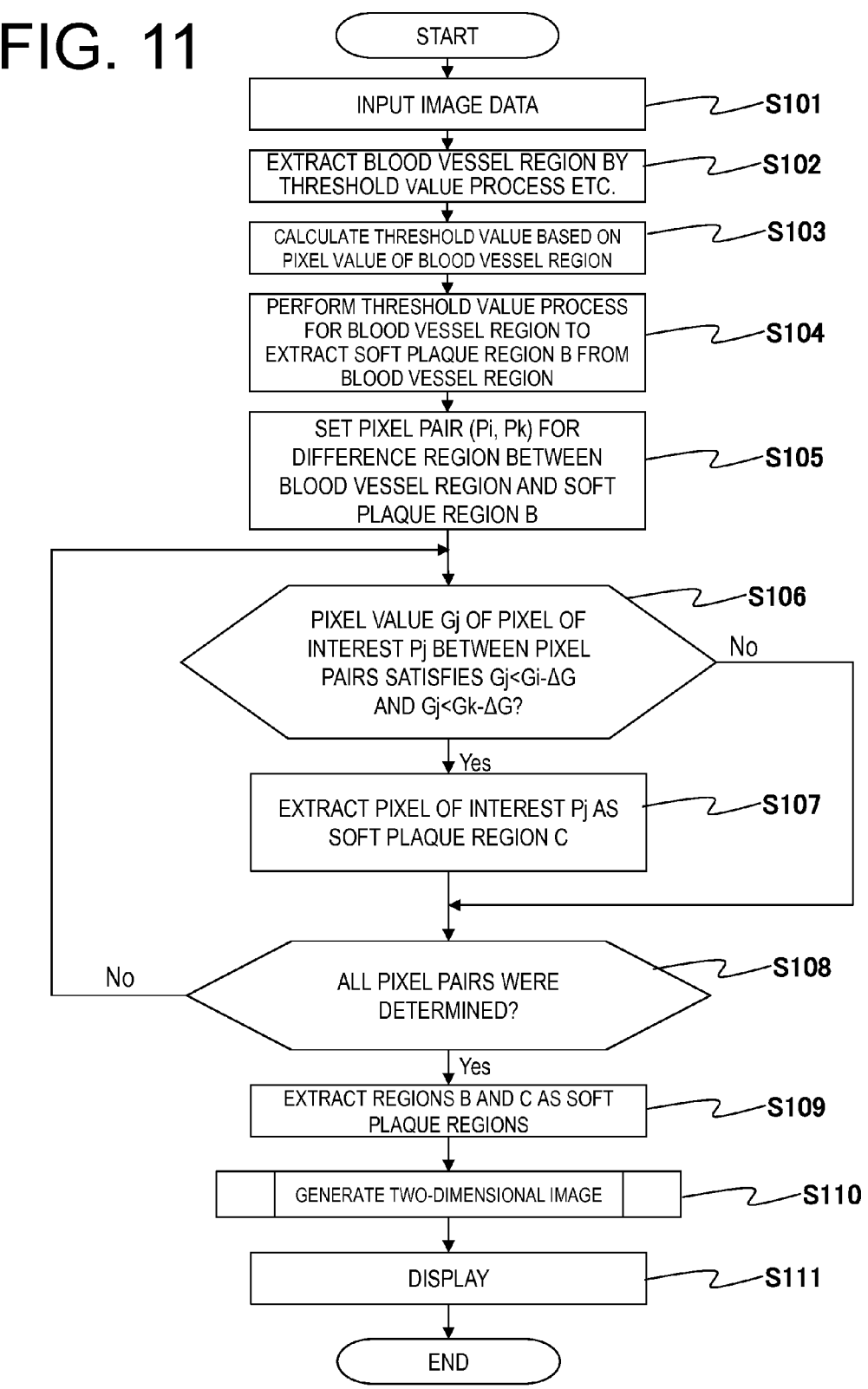
FIG. 11 is a flow chart explaining the procedure for the region extraction process related to the present invention.
Figure 13:
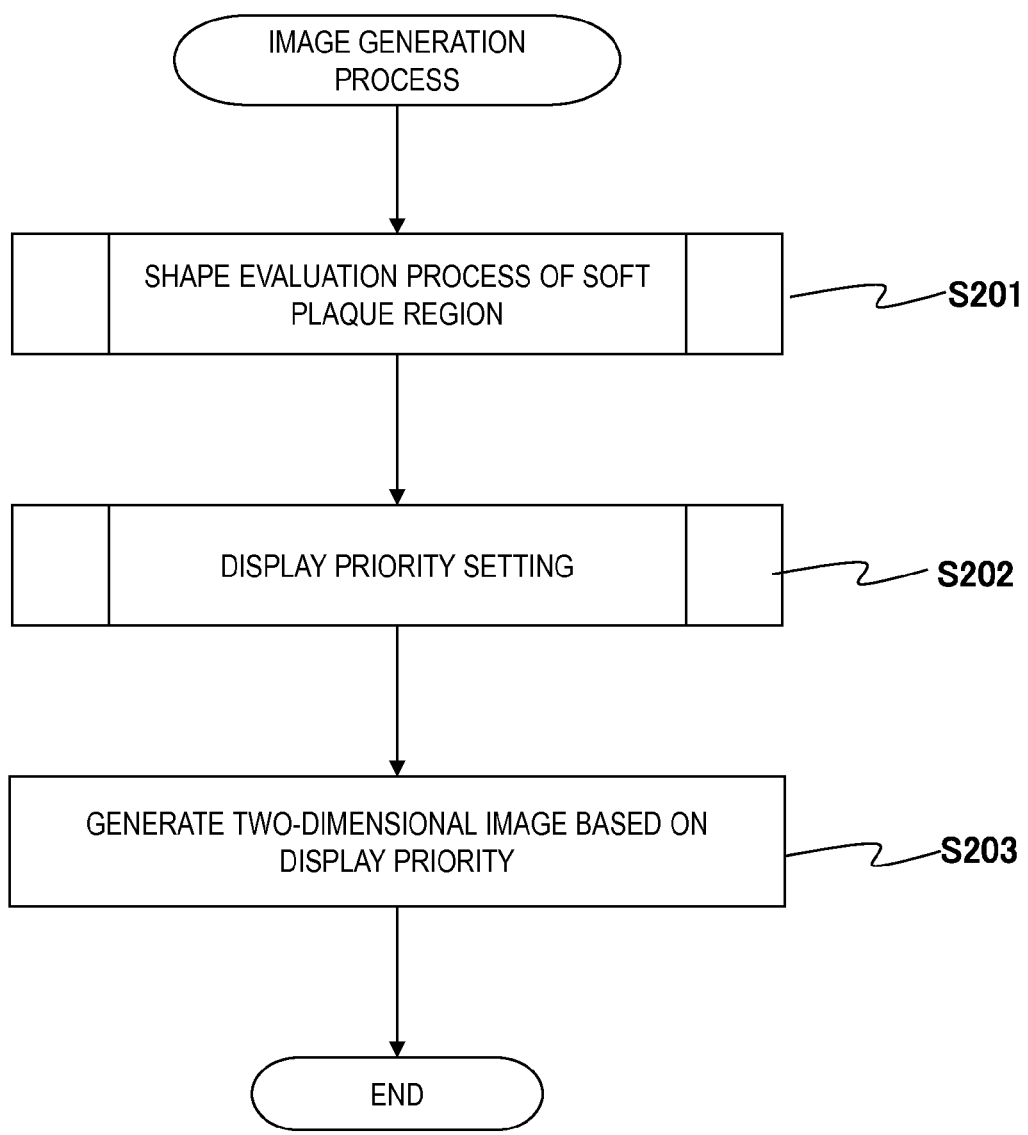
FIG. 13 is a flow chart explaining the procedure for the image generation process.

Additionally, for example, a blood vessel region and a soft plaque region have been extracted from an image to be a target for the image generation process of FIG. 13 in the same procedure as the region extraction process of the first embodiment (Steps S101 to S109 of FIG. 11).

The CPU 101 executes a shape evaluation process of a soft plaque region (Step S201). The shape evaluation process is performed according to the procedure (shape evaluation process (1)) shown in FIG. 14, for example.

Figure 14:
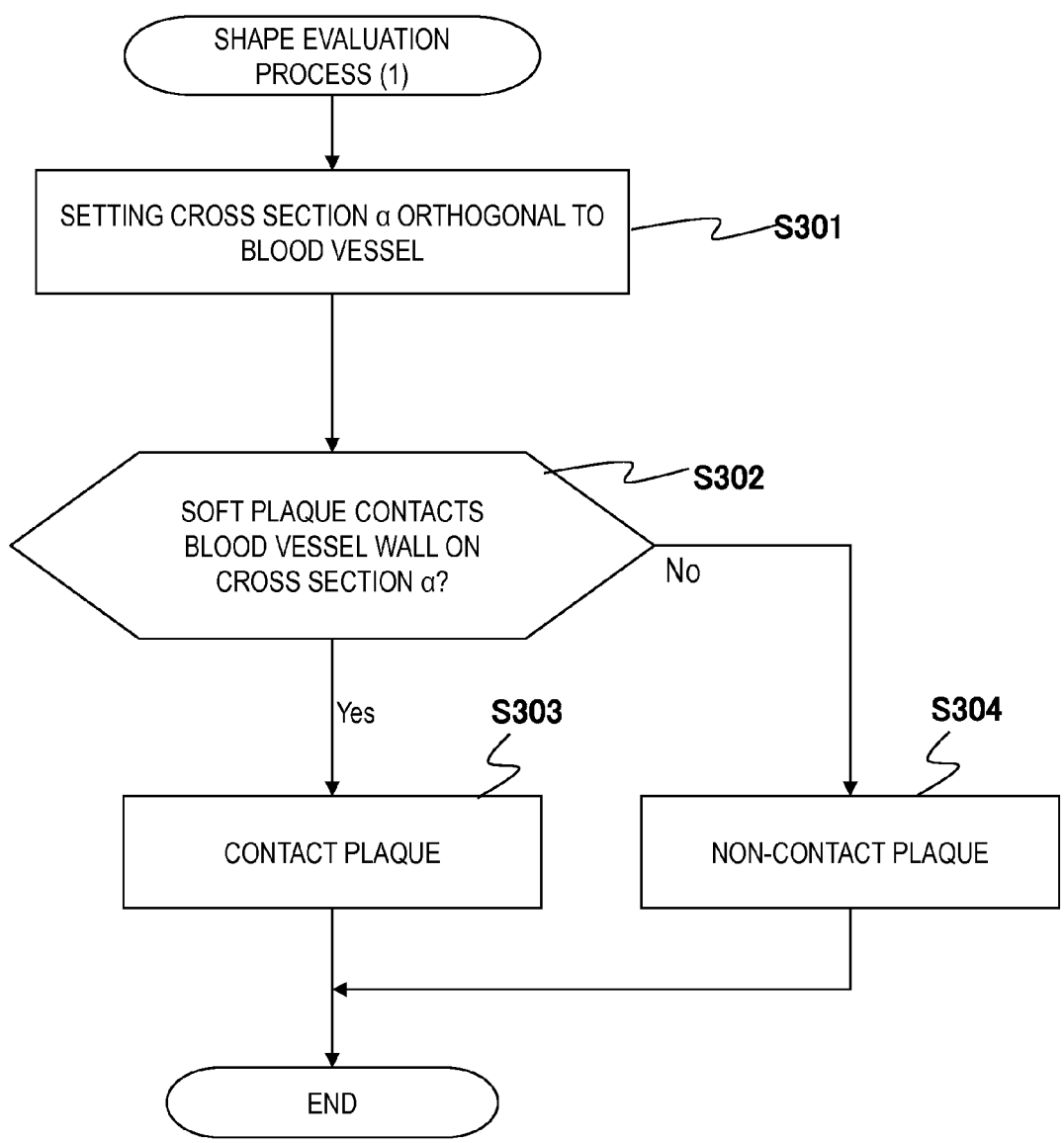
FIG. 14 is a flow chart explaining the procedure for the shape evaluation process (1).

In the shape evaluation process (1) shown in FIG. 14, the CPU 101 (the soft plaque shape evaluation section 274) first sets the cross section α orthogonal to the blood vessel 5 (Step S301). The CPU 101 determines whether or not a soft plaque region in the cross section α comes into contact with the blood vessel wall 51 (Step S302). Whether or not the soft plaque region comes into contact with the blood vessel wall 51 is determined based on the surrounding pixel values of the soft plaque region. In a case where there are pixels that are not pixel values of blood in the surroundings, a result in which the said soft plaque region is the contact plaque 52 is returned (Step S302: Yes→Step S303). In a case where all the surrounding pixels of the soft plaque region are pixel values of blood, a result in which the soft plaque region is the non-contact plaque 53 is returned (Step S302: No→Step S304).

The procedure goes back to Step S202 in the image generation process of FIG. 13. In Step S202, the CPU 101 performs a display priority setting process based on a shape evaluation result of soft plaque. The display priority setting process, for example, is performed in the procedure shown in FIG. 15.

Figure 15:
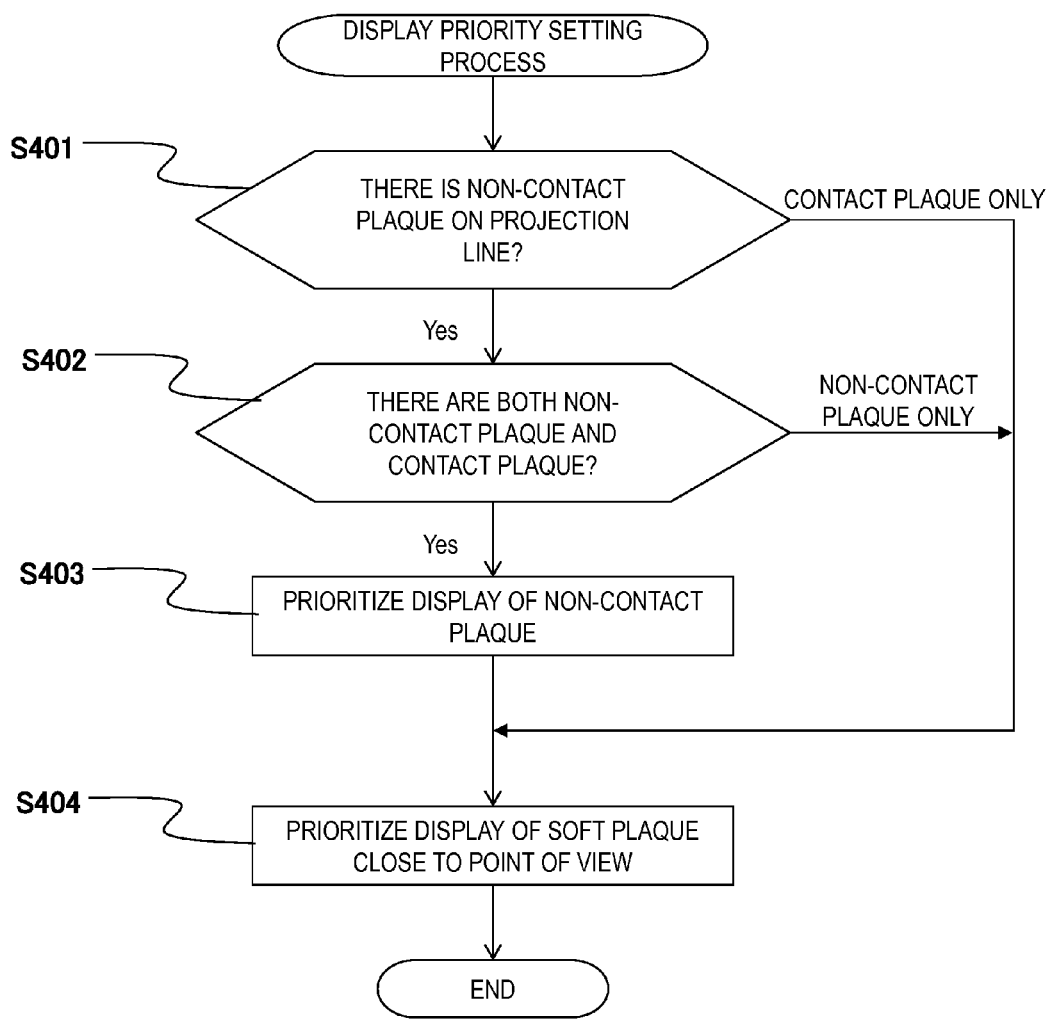
FIG. 15 is a flow chart explaining the procedure for the display priority setting process.

Additionally, when starting the display priority setting process of FIG. 15, a projection plane and a view position should be set.

The CPU 101 determines whether or not there is the non-contact plaque 53 on the projection line 69 (Step S401). In a case where there is the non-contact plaque 53 on the projection line 69 (Step S401: Yes), the CPU 101 further determines whether or not there are the non-contact plaque 53 and the contact plaque 52 on the projection line 69 (Step S402). In a case where there are the non-contact plaque 53 and the contact plaque 52 on the projection line 69 (Step S403: Yes), a display of the non-contact plaque 53 is prioritized (Step S403). Also, in case of the non-contact plaque 53 only (Step S402: non-contact plaque only), a display of the non-contact plaque 53 close to the point of view is prioritized (Step S404).

In a case where there is only the contact plaque 52 without the non-contact plaque 53 on the projection line 69 (Step S401: contact plaque only), a display of soft plaque close to the point of view is prioritized (Step S404).

After a display priority setting process is performed for each blood vessel orthogonal cross section α in such a procedure, the procedure goes back to the Step S203 process of FIG. 13. The CPU 101 generates a two-dimensional image based on the set display priority (Step S203).

Figure 12:
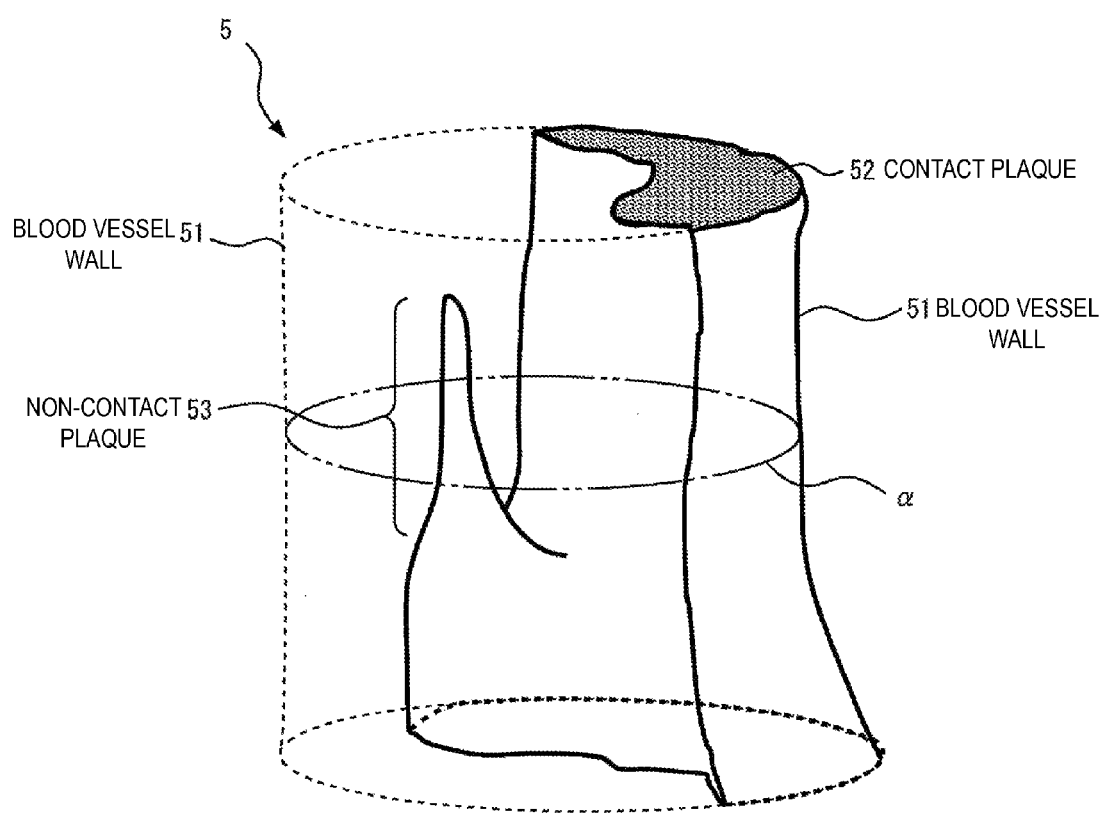
FIG. 12 is an explanatory diagram of the shape and type of soft plaque in the blood vessel 5.

FIGS. 16 to 19 show the relationship between the soft plaque arrangement and the projected image in the orthogonal cross section α (α1 to α4) of the blood vessel 5 shown in FIG. 12. The projection plane 60 is, for example, a vertical plane to the blood vessel orthogonal cross section α (α1 to α4). The point of view is provided in a position opposite to the projection plane 60 via the blood vessel 5. An example of parallel projecting the blood vessel 5 to the projection plane 60 is shown. The projection method may be MIP, 3D, ray-sum, or the other method.

A display priority of the non-contact plaque 53 that does not come into contact with the blood vessel wall 51 is set higher than the other regions. The CPU 101 projects soft plaque to the projection plane 60 from a predetermined projection direction to generate a projection image.

Figure 16:
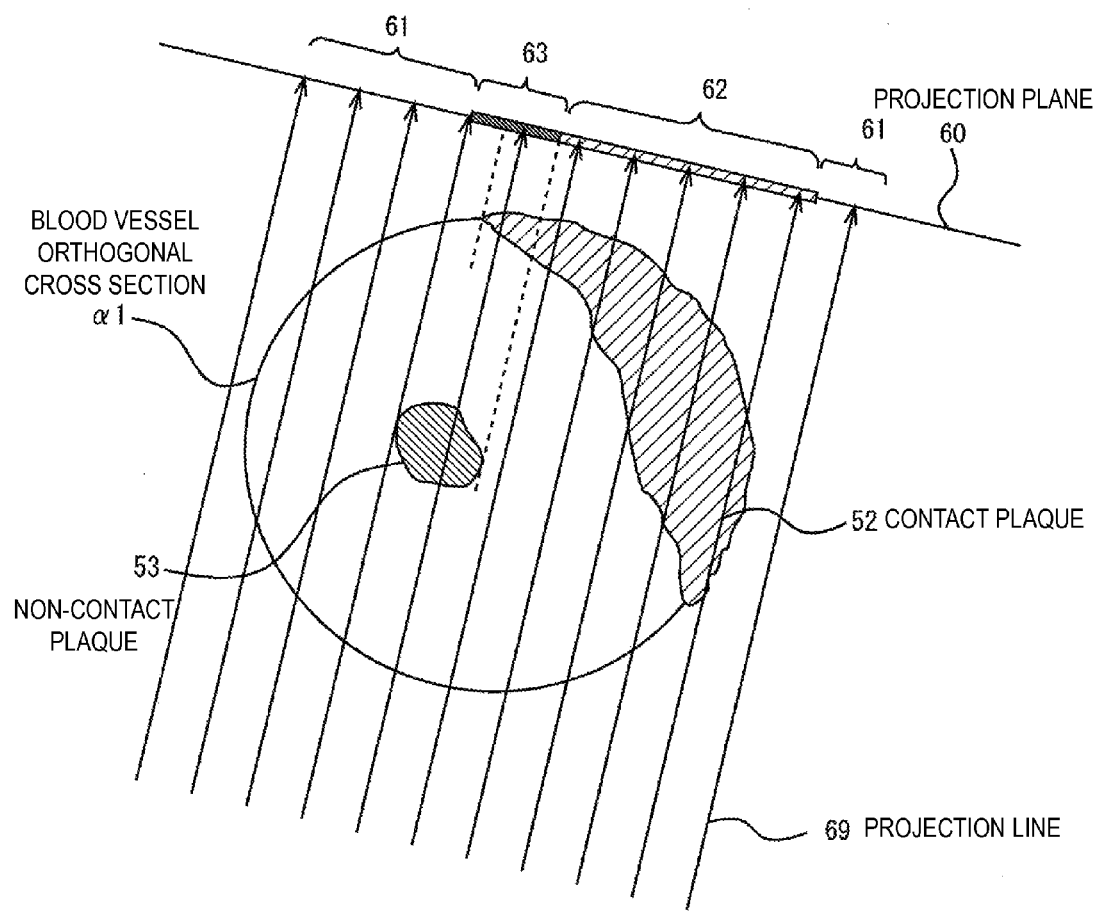
FIG. 16 is an explanatory diagram of drawing according to the display priority set based on the soft plaque shape (in a case where the non-contact plaque 53 and the contact plaque 52 exist).

There are the non-contact plaque 53 and the contact plaque 52 in the cross section α1 shown in FIG. 16. In this case, the non-contact plaque 53 is prioritized over the contact plaque 52 when projected to the projection plane 60. Also, it is desirable to use red for the projected image 63 of the non-contact plaque 53 as a display color when showing that the pathological risk is high. Specifically, the projected image 63 corresponding to the non-contact plaque 53 is color-coded in red, and the projected image 62 corresponding to the contact plaque 52 is color-coded in green.

Contrasted blood is drawn rather than soft plaque because a maximum pixel value on a projection line is projected in a normal MIP process, which results in that the soft plaque cannot be found on a projected image, but the non-contact plaque 53 is drawn due to the image generation process of the present embodiment. An operator can check the non-contact plaque 53 on an MIP image. Also, a pathological risk can be observed intuitively by color-coding.

Figure 17:
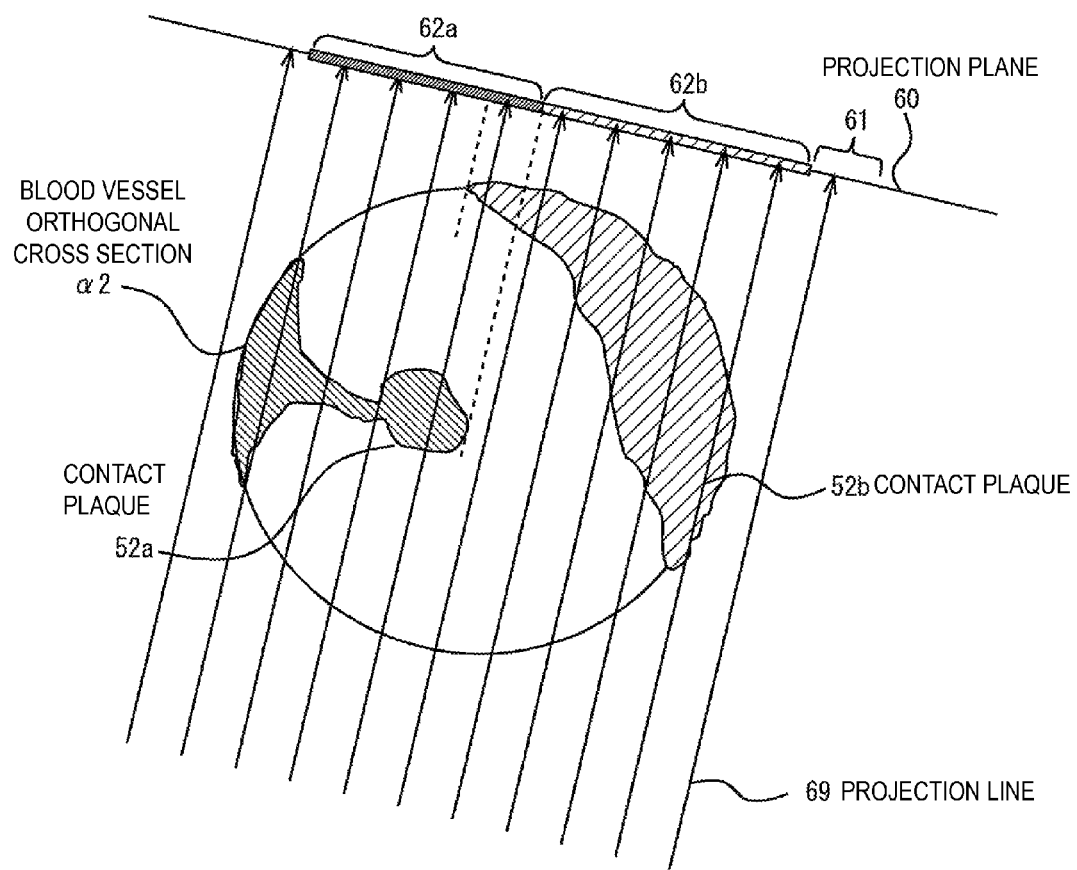
FIG. 17 is an explanatory diagram of drawing according to the display priority set based on the soft plaque shape (in a case where a plurality of the contact plaque 52a and 52b exist).

There is not the non-contact plaque 53 in the cross section α2 shown in FIG. 17, there are a plurality of the contact plaque 52a and 52b. In this case, a display priority of the contact plaque 52a closer to the point of view is set higher. Specifically, the CPU 101 projects the projected image 62a of the contact plaque 52a closer to the point of view so that it is positioned in front of the projected image 62b corresponding to the other contact plaque 52b. Also, colors of the projected images 62a and 62b should be different in color intensity and brightness even in the same green, which can indicate a state where a plurality of regions are superimposed and projected.

Figure 18:
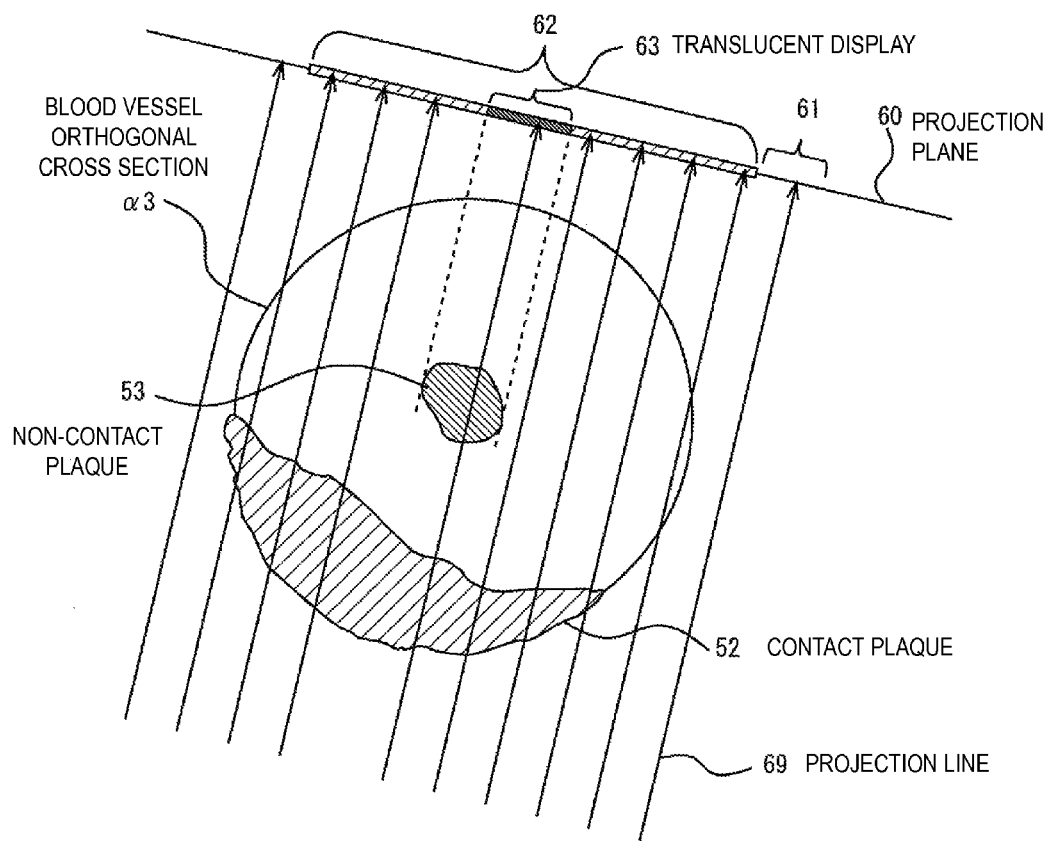
FIG. 18 is an explanatory diagram of drawing according to the display priority set based on the soft plaque shape (in a case where the non-contact plaque 53 and the contact plaque 52 exist).

There are the non-contact plaque 53 and the contact plaque 52 in the cross section α3 shown in FIG. 18. Also, the contact plaque 52 is positioned closer to the point of view than the non-contact plaque 53 on the projection line 69. In this case, the projected image 63 of the non-contact plaque 53 is displayed in a translucent color, a dashed line, or the like in the projected image 62 of the contact plaque 52. Hence, it can be indicated that there is the non-contact plaque 53 on the projection line even though it is hidden from the point of view.

Figure 19:
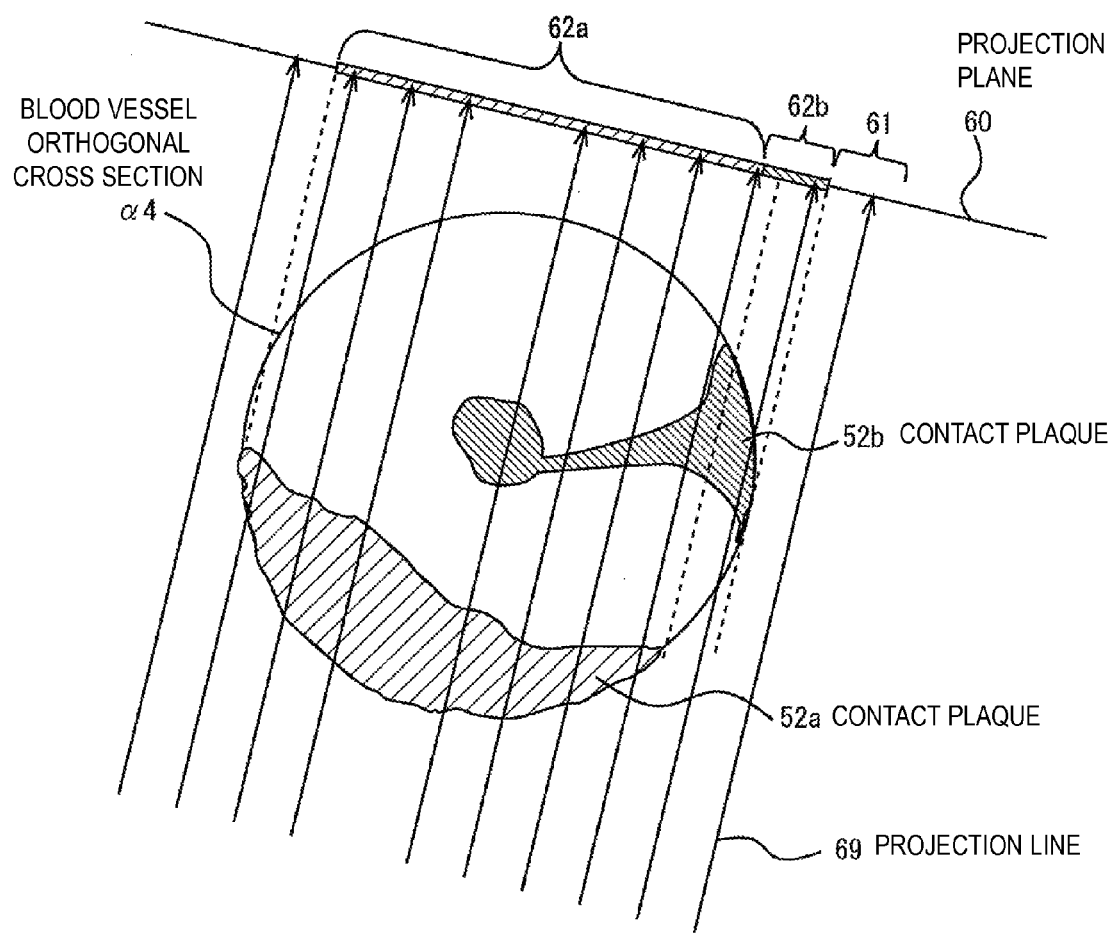
FIG. 19 is an explanatory diagram of drawing according to the display priority set based on the soft plaque shape (in a case where a plurality of the contact plaque 52a and 52b exist).

There is not the non-contact plaque 53 in the cross section α4 shown in FIG. 19. There are the contact plaque 52a and the contact plaque 52b in two positions. In this case, similarly to the example of FIG. 17, a display priority of the contact plaque 52a closer to the point of view is set higher than the other contact plaque 52b. Also, the projected image 62a of the contact plaque 52a closer to the point of view is projected so that it is positioned in front of the projected image 62b corresponding to the other contact plaque 52b. Colors of the respective projected images 62a and 62b should be different in color intensity and brightness even in the same green, which can indicate a state where there are a plurality of regions and they are superimposed.

Figure 20:
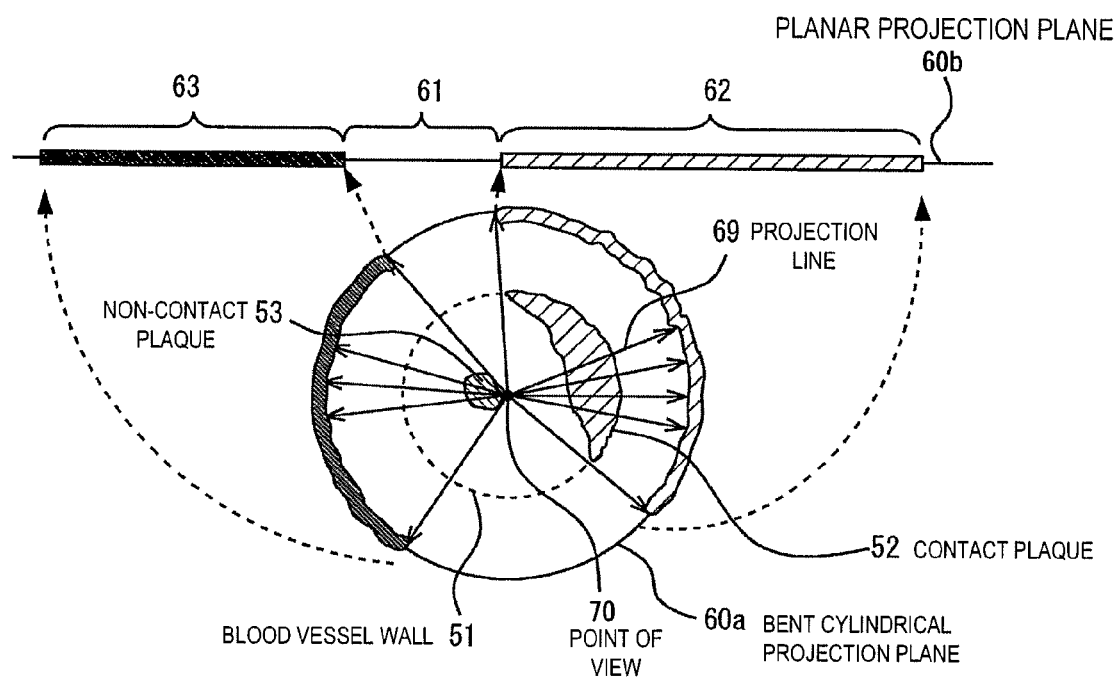
FIG. 20 is a drawing example of setting the point of view 70 in the blood vessel.

FIG. 20 shows an example of central projection. In the central projection, the CPU 101 sets the point of view 70 inside a blood vessel and the bent cylindrical projection plane 60a along the blood vessel shape around the blood vessel. Additionally, the image of the bent cylindrical projection plane 60a is developed on the planar projection plane 60b.

Similarly to FIG. 16 even in case of central projection, the projected image 63 corresponding to the non-contact plaque 53 is drawn in red, and the projected image 62 corresponding to the contact plaque 52 is drawn in green. Hence, the non-contact plaque 53 and the risk can be easily checked visually.

In a case where there are the contact plaque 52 and the non-contact plaque 53 on the projection line 69, a display priority of the non-contact plaque 53 is set higher than the other.

FIG. 21 shows an example of an image generated in the second embodiment. The image 45 of FIG. 21(a) is synthesized and displayed by shading the soft plaque region 45c in a certain blood vessel 45b on the MIP image 451 generated using the original CT image (three-dimensional original image). The partial region 45d in the soft plaque region 45c is displayed in a display color or a display format different from the other regions. The region 45d shows the non-contact plaque 53. In an actual image, it is desirable to draw in a red color, for example. The other soft plaque region 45c is the contact plaque 52, and it is desirable to draw in a green color in an actual image.

The image 46 of FIG. 21(b) is synthesized and displayed by shading the soft plaque region 46c in a certain blood vessel 46b on the boning MIP image 461 generated using the original CT image (three-dimensional original image). The partial region 46d in the soft plaque region 46c is displayed in a display color or a display format different from the other regions. The region 46c shows the non-contact plaque 53. In an actual image, it is desirable to draw in a red color, for example. The other soft plaque region 46c is the contact plaque 52, and it is desirable to draw in a green color in an actual image. In the boning MIP image 461, the calcified region 46e of an artery blood vessel etc. is also drawn. In the image 46, the calcified region 46e as well as the soft plaque region 46c and 46d can be observed simultaneously.

As described above, the image processing device 100 of the second embodiment determines a soft plaque region shape and sets a high display priority for the non-contact plaque 53 to generate a two-dimensional image. Also, the non-contact plaque 53 is drawn in a red color and the contact plaque 52 is drawn in a green color to display them in different colors. Hence, it can be clearly and intuitively shown that there is the non-contact plaque 53 with a high risk.

Third Embodiment

Figure 25:
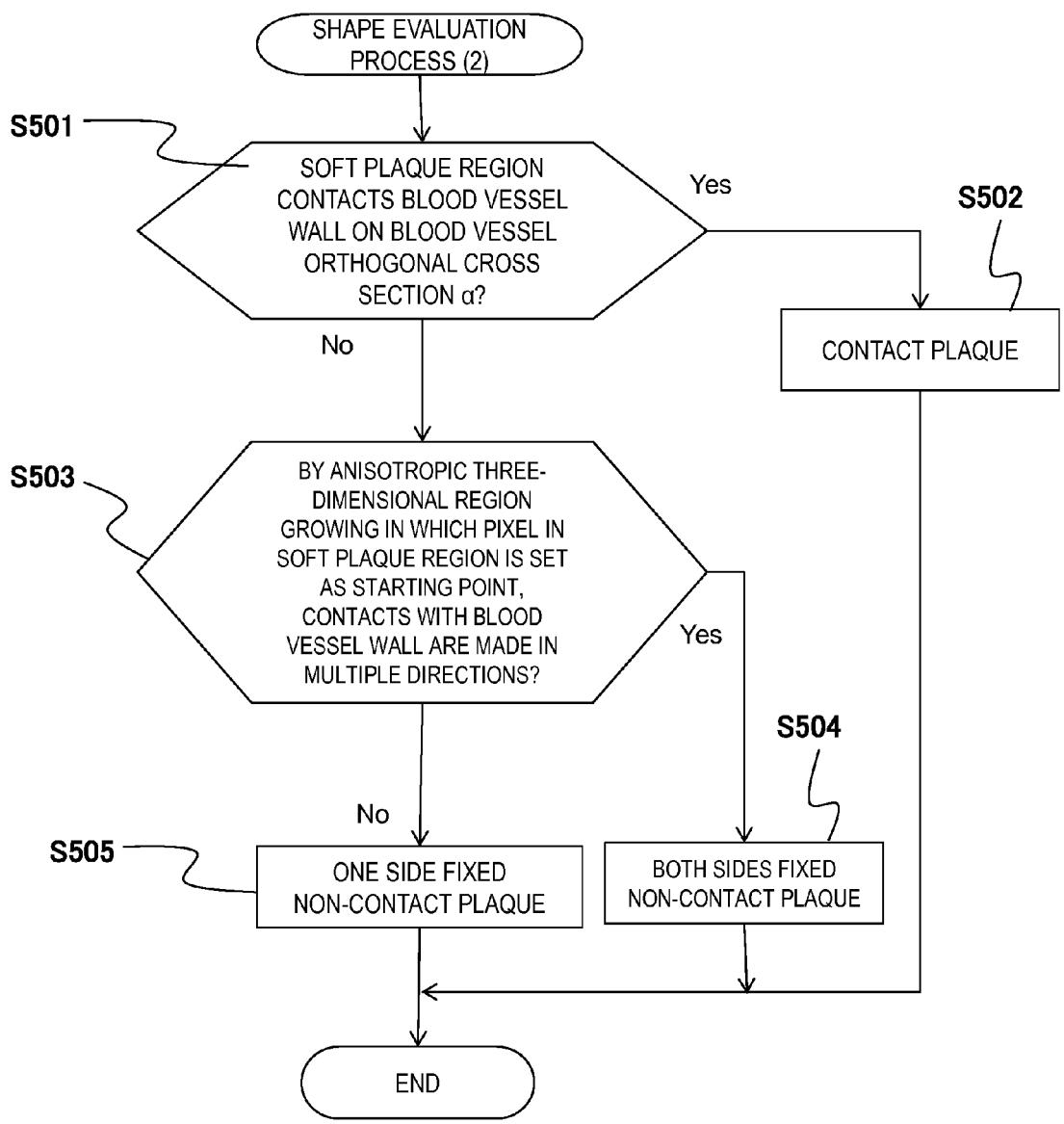
FIG. 25 is a flow chart explaining the procedure for the shape evaluation process (2).

In the third embodiment, the soft plaque shape evaluation process (2) shown in FIG. 25 is performed instead of the soft plaque shape evaluation process (2) of the second embodiment (see FIG. 14).

In the soft plaque shape evaluation process (2) of the third embodiment, a three-dimensional shape of the non-contact plaque 53 will be analyzed. Specifically, soft plaque that was determined as the non-contact plaque 53 in a cross section will be determined whether or not the soft plaque comes into contact with a blood vessel wall and the other soft plaque in the other cross section.

Figure 22:
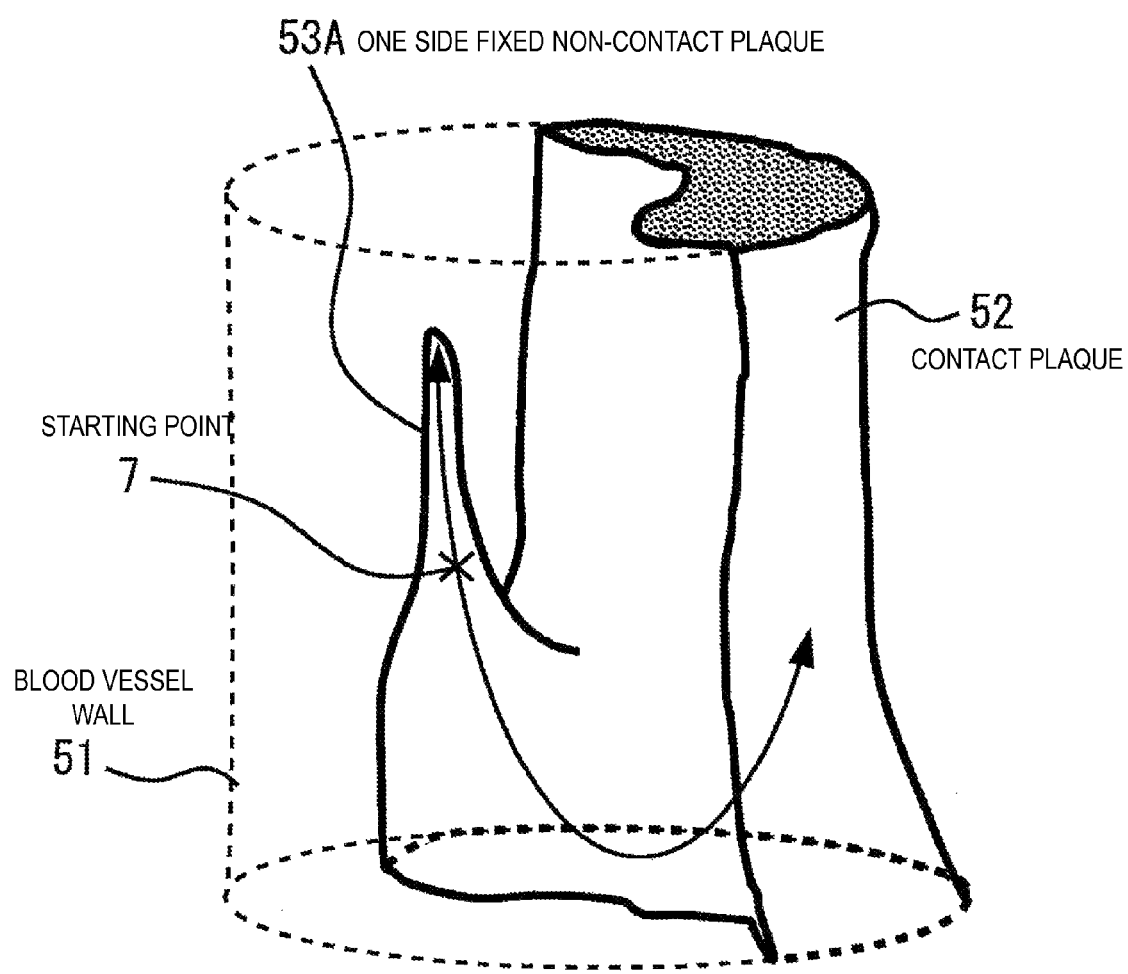
FIG. 22 is an explanatory diagram of the one side fixed non-contact plaque 53A.
Figure 23:
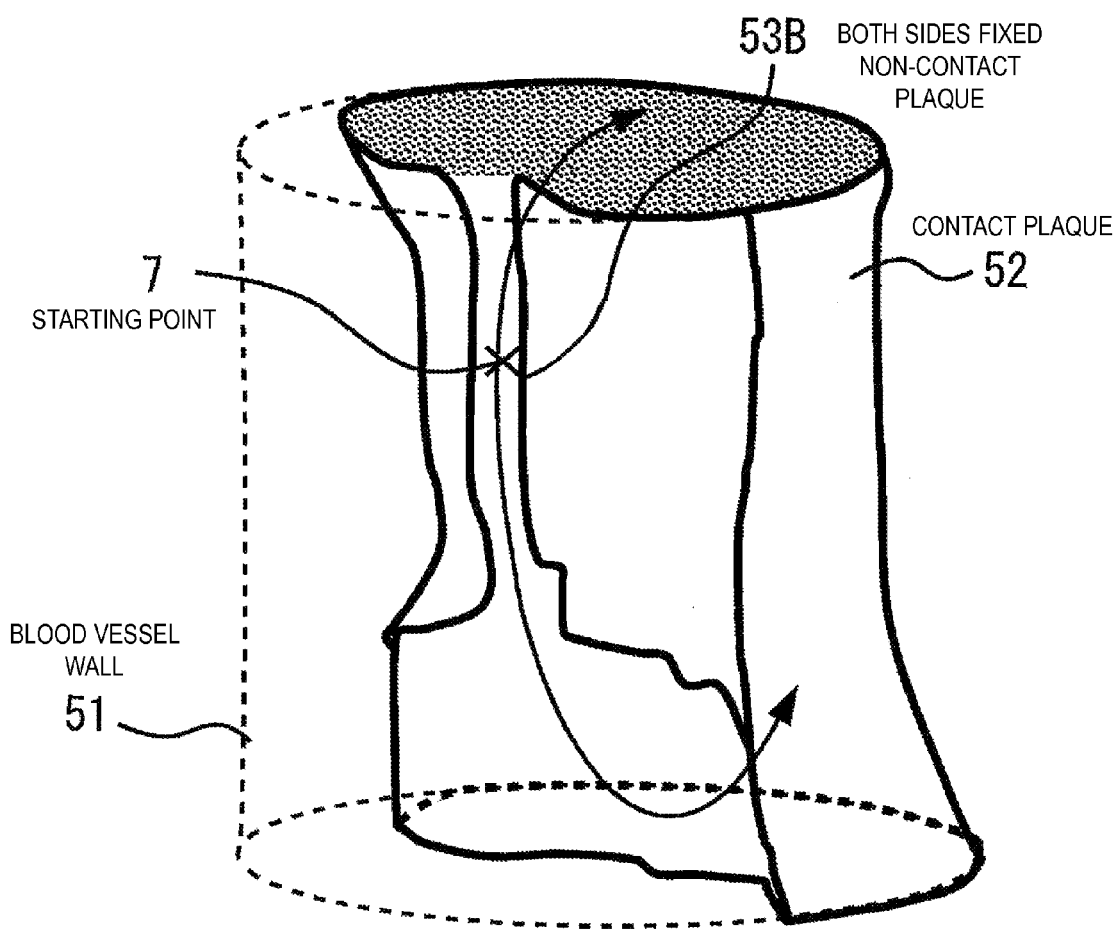
FIG. 23 is an explanatory diagram of the both sides fixed non-contact plaque 53B.
Figure 24:
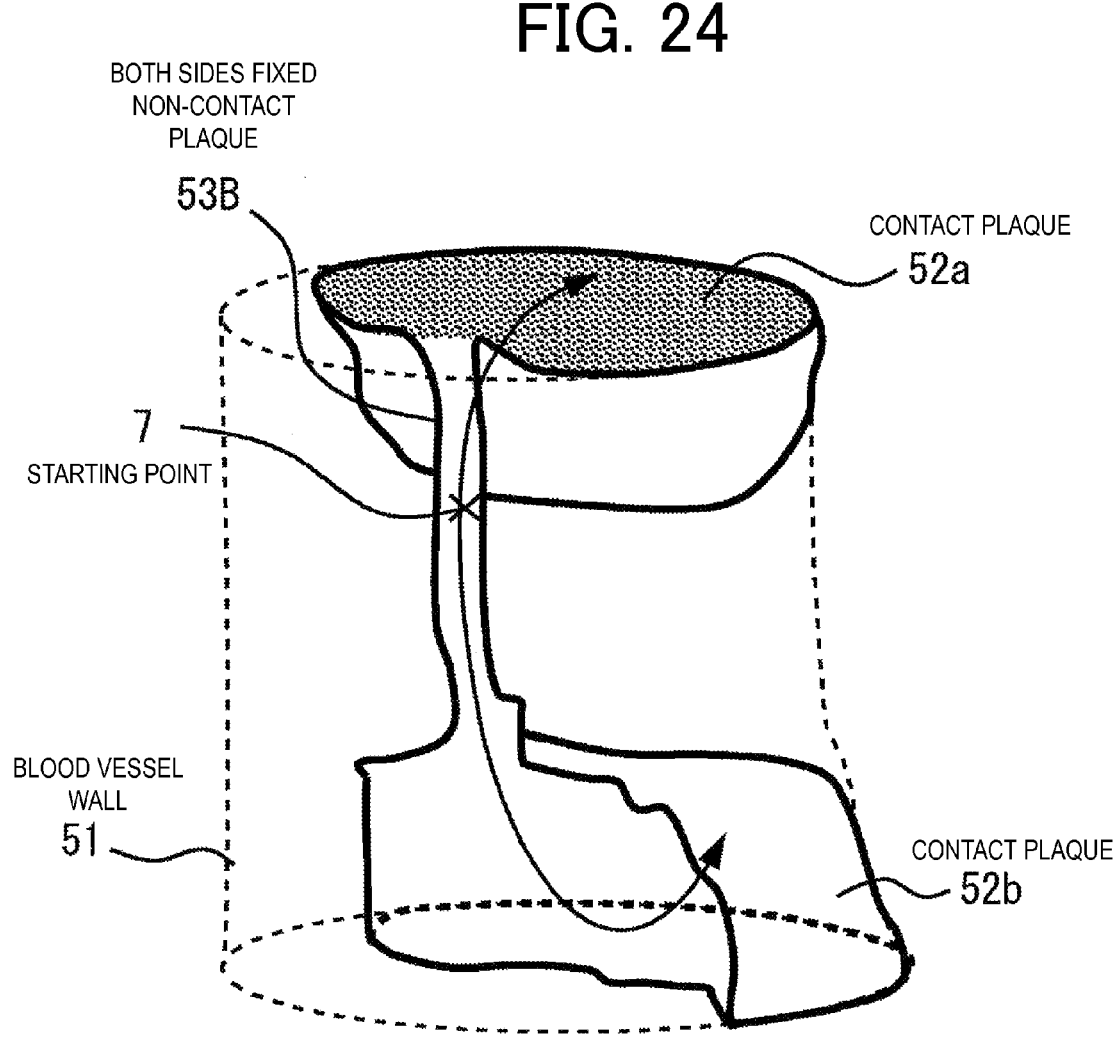
FIG. 24 is an explanatory diagram of the other example of the both sides fixed non-contact plaque 53B.

Referring to FIGS. 22 to 24, soft plaque shapes will be described. The non-contact plaque shown in FIG. 22 has one end reaching and adhering to the contact plaque 52 and the other end that does not come into contact. Hereinafter, the soft plaque with such a shape is referred to as the one side fixed non-contact plaque 53A.

Both the sides of the non-contact plaque shown in FIG. 23 reach and adhere to the contact plaque 52. Hereinafter, the soft plaque with such a shape is referred to as the both sides fixed non-contact plaque 53B. There is a case where the contact plaque 52a and the contact plaque 52b are separated into two positions; the non-contact plaque has one end adhering to the contact plaque 52a and the other end adhering to the contact plaque 52b as the soft plaque shown in FIG. 24. Such a shape is also referred to as the both sides fixed non-contact plaque 53B.

In order to analyze a three-dimensional shape of soft plaque, the shape evaluation process (2) shown in FIG. 25 is executed in the third embodiment.

Hereinafter, the shape evaluation process (2) will be described.

First, the CPU 101 determines whether or not soft plaque comes into contact with the blood vessel wall 51 in the blood vessel orthogonal cross section α (Step S501). In case of coming into contact with the blood vessel wall 51 (Step S501: Yes), it is determined as the contact plaque 52 (Step S502). If the soft plaque does not come into contact with the blood vessel wall 51 in the blood vessel orthogonal cross section α (Step S501: No), the procedure proceeds to Step S503.

The CPU 101 performs an anisotropic three-dimensional region growing process by setting an arbitrary pixel in the soft plaque of interest as the starting point 7. Region growing is performed by the anisotropic three-dimensional region growing process to determine whether or not to come into contact with a blood vessel wall or the contact plaque 52 in all the directions (at least two or more directions) (Step S503).

For example, as shown in the non-contact soft plaque of FIG. 22, although a region growing process ends without a contact when performing the process in one direction from the starting point 7, the region growing process in the other direction from the starting point 7 results in reaching the contact plaque. Thus, when the non-contact soft plaque in a cross-section is viewed three-dimensionally, the plaque is fixed to (comes into contact with) one side and does not come into contact with the other side, which results in that the plaque is the one side fixed non-contact plaque 53A (Step S505).

Also, as shown in FIGS. 23 and 24, when a region growing process is performed in the two opposite directions from the starting point 7 and both the directions reach the contact plaque 52 (Step S503: Yes), which results in that the plaque is the both sides fixed non-contact plaque (Step S504). As a difference between FIGS. 23 and 24, while the non-contact plaque 53 is fixed to a chunk of the contact plaque 52 in FIG. 23, the non-contact plaque 53 is fixed to the other chunks of the contact plaque 52a and the contact plaque 52b respectively in FIG. 24.

As shown in FIGS. 23 and 24, when at least two or more directions reach the contact plaque 52 in a case where an anisotropic three-dimensional region growing process is performed in a plurality of directions, even the non-contact plaque has a low risk to come off. Therefore, the CPU 101 draws the both sides fixed non-contact plaque 53B, for example, in a yellow color.

On the other hand, when the region growing ends without reaching the contact plaque 52 in any of the directions in a case where an anisotropic three-dimensional region growing is performed in a plurality of directions (the one side fixed non-contact plaque 53A of FIG. 53A), a risk to come off becomes the highest. Therefore, the one side fixed non-contact plaque 53A is drawn, for example, in a red color.

As described above, in the third embodiment, a three-dimensional shape of the non-contact plaque 53 is analyzed to determine whether or not the end is fixed to contact plaque. Then, different display colors etc. are used for drawing between when being fixed to one side and when being fixed to both sides. By evaluating whether or not to be a shape that has a high risk of soft plaque coming off, the display can be color-coded according to the shape.

Although suitable embodiments of an image processing device etc. related to the present invention were described above by referring to the attached diagrams, the present invention is not limited to such examples. For example, although processes for extracting soft plaque from a blood vessel were described in the above embodiments, images of the other internal organs may be the targets. It is apparent that a person skilled in the art could arrive at modified examples or amended examples within the scope of the technical ideas disclosed in the present invention, and it is understood that these naturally belong to the technical scope of the present invention.

DESCRIPTION OF REFERENCE NUMERALS

1: image processing system
100: image processing device
101: CPU
102: main memory
103: storage device
104: communication I/F
105: display memory
106: I/F
107: display device
108: mouse
109: input device
110: network
111: image database
112: medical image scanning device
113: bus
21: input unit
22: first region extracting unit
23: threshold value calculating unit
24: second region extracting unit
25: third region extracting unit
251: difference region calculation section
252: pixel pair setting section
253: comparison section
26: target region setting unit
27: image generating unit
271: synthesized image generation section
272: rate display section
273: cross-section image display section
274: soft plaque shape evaluation section
275: display priority setting section
28: display unit
A: blood vessel region (first region)
B: soft plaque region (second region)
C: soft plaque region (third region)
52: contact plaque
53: non-contact plaque
53A: one side fixed non-contact plaque
53B: both sides fixed non-contact plaque
60: projection plane

The invention claimed is:

1. An image processing device comprising:
an input unit for inputting image data, wherein the image data is a three-dimensional original image;
a first region extracting unit for extracting a first region from the image data input by the input unit;
a second region extracting unit for performing a threshold value process for the first region using a threshold value based on a concentration in the first region to extract a second region from the first region;
a third region extracting unit for setting a pixel pair that is a combination of two pixels in a difference region between the first and second regions; setting pixels between each pixel pair as pixels of interest; and then extracting the pixel of interest as a third region in a case where a difference between a pixel value of the pixel of interest and at least either pixel value of the pixel pair is larger than a predetermined value;
a target region setting unit for obtaining a region where the second and third regions are added as a target region;
a shape evaluation section for determining whether or not the target region comes into contact with the inner periphery of the first region;
an image generating unit for generating that sets a display priority based on a determination result of the shape evaluation section, and generates a two-dimensional image of the range including the target region and the surroundings, based on the three-dimensional original image and the display priority;
a display unit for displaying the two-dimensional image generated by the image generating unit,
wherein the image generating unit sets a higher display priority in a case where the target region does not come into contact with the inner periphery of the first region than in a case that the target region comes into contact with the inner periphery of the first region and sets a higher display priority when one side of the target region does not adhere to a contact region which comes into contact with the inner periphery of the first region than when both side of the target region adhere to the contact region.

2. The image processing device according to claim 1, wherein the first region is a blood vessel region, and the target region is a soft plaque region.

3. The image processing device according to claim 1, wherein the image generating unit generates a reference two-dimensional image of the surroundings of the target region as well as a shaded image of the target region, and generates the shaded image of the target region is superimposed or synthesized on the reference two-dimensional image to generate the synthesized image.

4. The image processing device according to claim 3, comprising:
   a position designation section for designating an arbitrary position of the synthesized image, and
   a cross-section image display section superimposes the target region on a cross-sectional image orthogonal to the first region in a designated position by the position designation section.

5. The image processing device according to claim 1, further comprising:
   a rate display section for displaying a rate at which the first region is occupied by the target region.

6. The image processing device according to claim 1, wherein the image processing device further sets a higher display priority when the target region is relatively closer to a point of view than when the target region is relatively further from the point of view.

7. An image processing device comprising:
   a blood vessel region extracting unit for extracting a blood vessel region from an image;
   a soft plaque region extracting unit for extracting a soft plaque region in the blood vessel region;
   a shape evaluation section for determining whether or not the soft plaque region comes into contact with a blood vessel wall;
   a display priority setting section that sets a display priority based on a determination result of the shape evaluation section, the display priority setting section setting a higher display priority in a case where the soft plaque region does not come into contact with the blood vessel wall than in a case that the soft plaque region comes into contact with the blood vessel wall, and setting a higher display priority when one side of the soft plaque region does not adhere to a contact plaque region which comes into contact with the blood vessel wall than when both side of the soft plaque region adhere to the contact plaque region; and
   an image generating unit for generating a two-dimensional image of the blood vessel region based on the display priority.

8. The image processing device according to claim 7, wherein the shape evaluation section determines whether or not the soft plaque region comes into contact with the blood vessel wall based on a cross-section image of the blood vessel region.

9. The image processing device according to claim 8, wherein the shape evaluation section further three-dimensionally searches each direction of the surroundings of the soft plaque region based on a three-dimensional original image of the blood vessel region and whether or not the soft plaque region extends and reaches the blood vessel wall.

10. A region extraction method extracting a target region from image data, by a computer configured by execution of one or more programs of computer readable instructions, including:
   a step (a) of extracting a blood vessel region from an image;
   a step (b) of extracting a soft plaque region in the blood vessel region;
   a step (c) of determining whether or not the soft plaque region comes into contact with a blood vessel wall;
   a step (d) of setting a display priority based on a determination result of (c), including setting a higher display priority in a case where the soft plaque region does not come into contact with the blood vessel wall than in a case that the soft plaque region comes into contact with the blood vessel wall, and setting a higher display priority when one side of the soft plaque region does not adhere to a contact plaque region which comes into contact with the blood vessel wall than when both side of the soft plaque region adhere to the contact plaque region; and
   a step of generating a two-dimensional image of the blood vessel region based on the display priority.

* * * * *